(12) United States Patent
Feng

(10) Patent No.: US 11,931,711 B2
(45) Date of Patent: Mar. 19, 2024

(54) MICROCAPSULE CLUSTERS

(71) Applicant: Encapsys, LLC, Appleton, WI (US)

(72) Inventor: Linsheng Feng, Menasha, WI (US)

(73) Assignee: Encapsys, LLC, Appleton, WI (US)

( * ) Notice: Subject to any disclaimer, the term of this patent is extended or adjusted under 35 U.S.C. 154(b) by 288 days.

(21) Appl. No.: 16/839,887

(22) Filed: Apr. 3, 2020

(65) Prior Publication Data

US 2020/0316551 A1 Oct. 8, 2020

Related U.S. Application Data

(60) Provisional application No. 62/828,773, filed on Apr. 3, 2019.

(51) Int. Cl.
*B01J 13/10* (2006.01)
*C08L 33/10* (2006.01)

(52) U.S. Cl.
CPC ............... *B01J 13/10* (2013.01); *C08L 33/10* (2013.01)

(58) Field of Classification Search
CPC .......... B01J 13/10; B01J 13/185; B01J 13/20; C08L 33/10; A01N 25/28; A61K 9/501; A61K 9/5026; C11D 3/505; C08F 265/02; C09D 135/00; C09D 133/14
See application file for complete search history.

(56) References Cited

U.S. PATENT DOCUMENTS

| 5,330,566 A | 7/1994 | Copeland |
| 2017/0273877 A1 * | 9/2017 | Sasaki .................... C11D 3/222 |

FOREIGN PATENT DOCUMENTS

WO WO-2016049456 3/2016

OTHER PUBLICATIONS

PCT International Search Report for PCT.
International Preliminary Report on Patentability for PCT.

* cited by examiner

Primary Examiner — Andrew J. Oyer
(74) Attorney, Agent, or Firm — Benjamin Mieliulis

(57) ABSTRACT

The present invention teaches a composition and process for irreversibly agglomerated charge stable core shell microcapsules, each microcapsule containing a benefit agent core material, which may be the same or different, the polymeric all or walls comprising one or more (meth)acrylate polymers, or optionally combinations with other polymers, along with a polyvalent cation. The capsules of the invention adhere better to surfaces, are more stable and are useful for delivery of benefit agents.

17 Claims, 9 Drawing Sheets

MICROCAPSULE CLUSTERS

FIELD OF THE INVENTION

This invention relates to microcapsule compositions and particularly to microcapsules delivering a benefit agent, and processes for making and using such compositions.

BACKGROUND OF THE INVENTION

Various processes for microencapsulation, and exemplary methods and materials are set forth in Schwantes (U.S. Pat. No. 6,592,990), Baker et. al. (U.S. Pat. No. 4,166,152), Matsukawa et. al. (U.S. Pat. No. 3,965,033), Matsukawa (U.S. Pat. No. 3,660,304), Ozono (U.S. Pat. No. 4,588,639), Irgarashi et. al. (U.S. Pat. No. 4,610,927), Brown et. al. (U.S. Pat. No. 4,552,811), Scher (U.S. Pat. No. 4,285,720), Shioi et. al. (U.S. Pat. No. 4,601,863), Kiritani et. al. (U.S. Pat. No. 3,886,085), Jahns et. al. (U.S. Pat. Nos. 5,596,051 and 5,292,835), Matson (U.S. Pat. No. 3,516,941), Chao (U.S. Pat. No. 6,375,872), Foris et. al. (U.S. Pat. Nos. 4,001,140; 4,087,376; 4,089,802 and 4,100,103), Greene et. al. (U.S. Pat. Nos. 2,800,458; 2,800,457 and 2,730,456), Clark (U.S. Pat. No. 6,531,156), Saeki et. al. (U.S. Pat. Nos. 4,251,386 and 4,356,109), Hoshi et. al. (U.S. Pat. No. 4,221,710), Hayford (U.S. Pat. No. 4,444,699), Hasler et. al. (U.S. Pat. No. 5,105,823), Stevens (U.S. Pat. No. 4,197,346), Riecke (U.S. Pat. No. 4,622,267), Greiner et. al. (U.S. Pat. No. 4,547,429), and Tice et. al. (U.S. Pat. No. 5,407,609), among others and as taught by Herbig in the chapter entitled "Microencapsulation" in Kirk-Othmer Encyclopedia of Chemical Technology, V. 16, pages 438-463.

More recently Schwantes U.S. Publication No. 2009/0274905 taught producing acrylic microcapsules from a reaction product of an amine with a multifunction (meth) acrylate, an oil soluble acid and initiator in the presence of a cationic emulsifier.

Attempts have been made to encapsulate perfumes in melamine formaldehyde shells along with a coating of polyvinyl formamide. In U.S. Pat. No. 8,759,275 Smet, et al., a coating of polyvinyl formamide acts as an efficiency polymer to facilitate more uniform deposition across a wide range of different substrates. The efficiency polymers can be formed by copolymerization of vinyl formamide with acrylamide, acrylic acid, acrylonitrile, ethylene, sodium acrylate, methyl acrylate, maleic anhydride, vinyl acetate and n-vinyl pyrrolidine, or by selective hydrolyzation of polyvinyl formamide.

In US 20130330292 Lei et al., polyurea microcapsules are formed by emulsification into a surfactant or treatment with salt then optionally followed by deposition aid addition.

WO 2016049456 Sasaki et al., combine cationic deposition aids to attempt to improve stability of the microcapsules with a binder polymer and one or more deposition polymers.

Although various encapsulation techniques are known, a need exists for capsules and particles which adhere to surfaces, which adhere longer or better. To provide formulators with better options, a need exists for improved microcapsules which are cationic, which can deliver benefit agents and/or adhere to anionic surfaces and which are more stable in terms of charge.

With certain capsules such as poly(meth)acrylate microcapsules, a continuing challenge is depositing or adhering such microcapsules efficiently, and minimizing leakage of benefit agent. Deposition aids are often relied upon. It would be an advance in the art to create capsule clusters in a controlled manner. It would be an advance in the art to create capsules which are more robust, have higher benefit agent retention or lower leakage. The invention surprisingly achieves desirable clustering of microcapsules. Clustering can be usefully employed to improve deposition by providing more efficient microcapsules. The microcapsules of the invention can employ a reduced mass of benefit agent while retaining similar or even better retention or delivery of benefit agent. The clusters for certain applications can reduce or even eliminate need for deposition aids, particularly when the clusters are charged clusters. Clustering in many applications improves benefit agent delivery as the clusters have a tendency to deposit and reside higher on surfaces, especially porous or fibrous surfaces, and therefore are more available. Agglomerates also are larger than the constituent component microcapsules, presenting or making available more benefit agent where needed. The clusters surprisingly benefit from the generally higher robustness of smaller capsules, but while at the same time benefiting from the advantage of a larger particulate. Loss of fines, such as into porous interstices of paper or fibers, can thereby also be minimized.

SUMMARY OF THE INVENTION

Figure 1A:
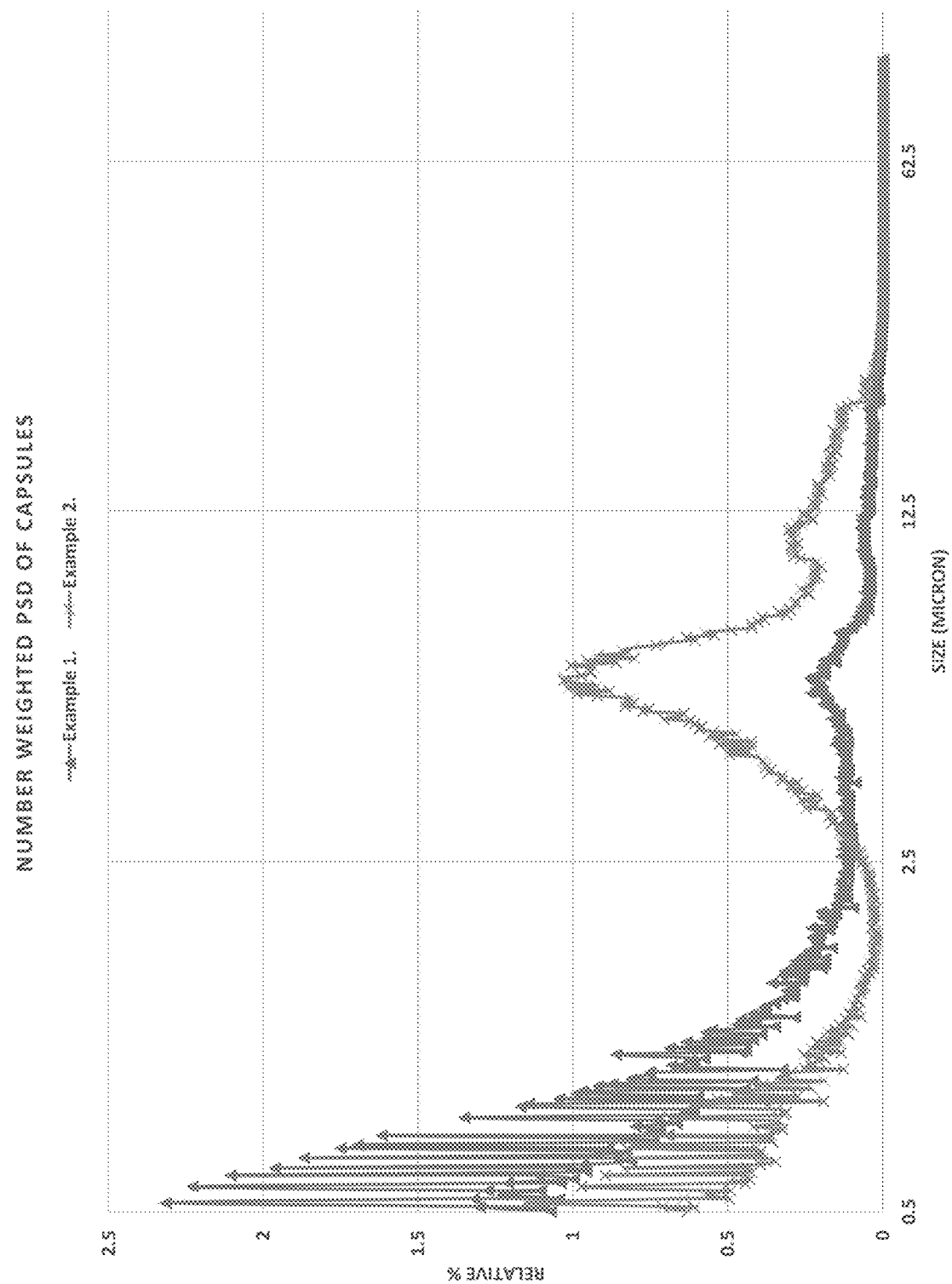
FIGS. 1A, 1B, 1C and 1D are graphs of the number weighted particle size distribution of Examples 1 through 7.
Figure 1B:
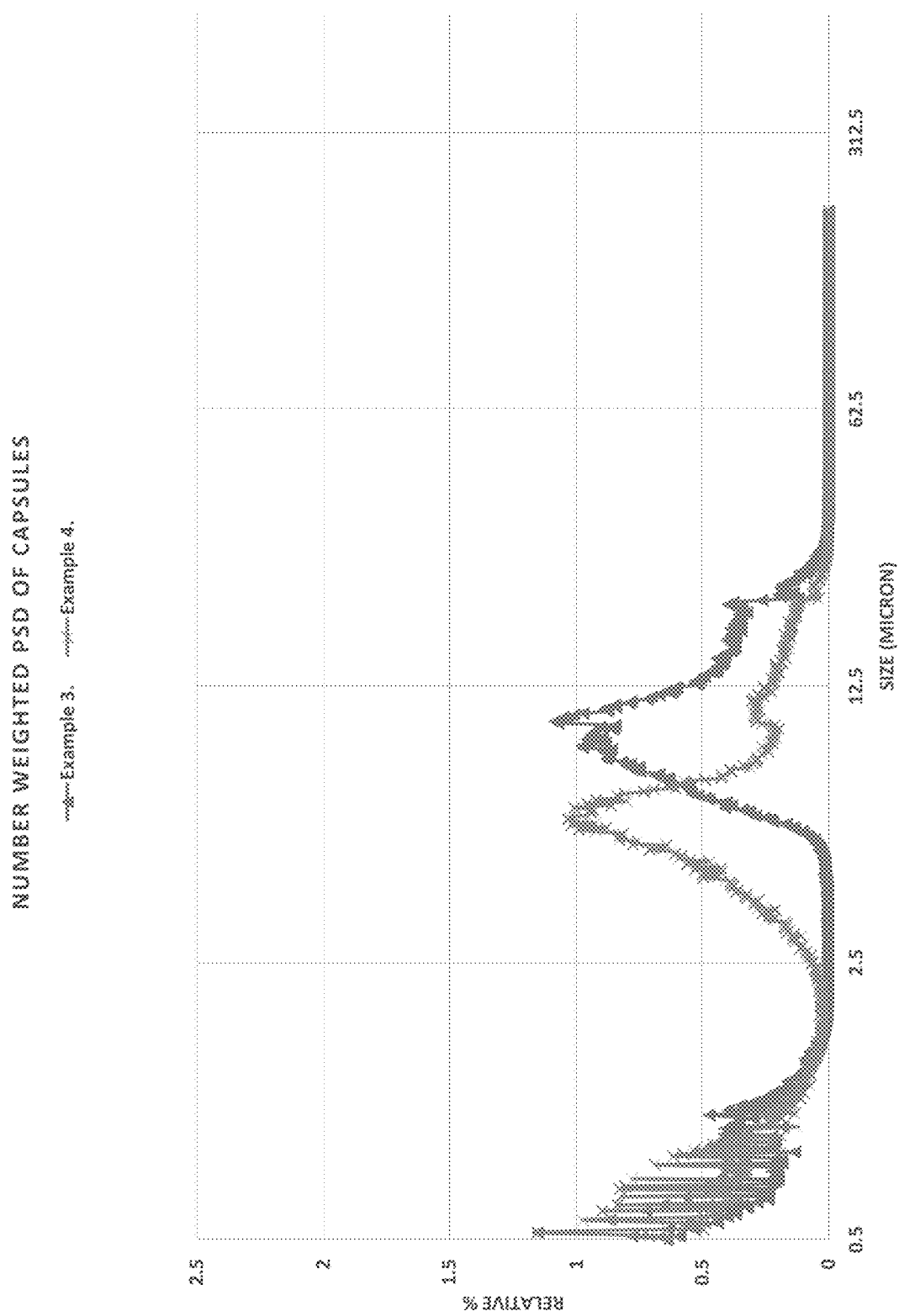
Figure 1C:
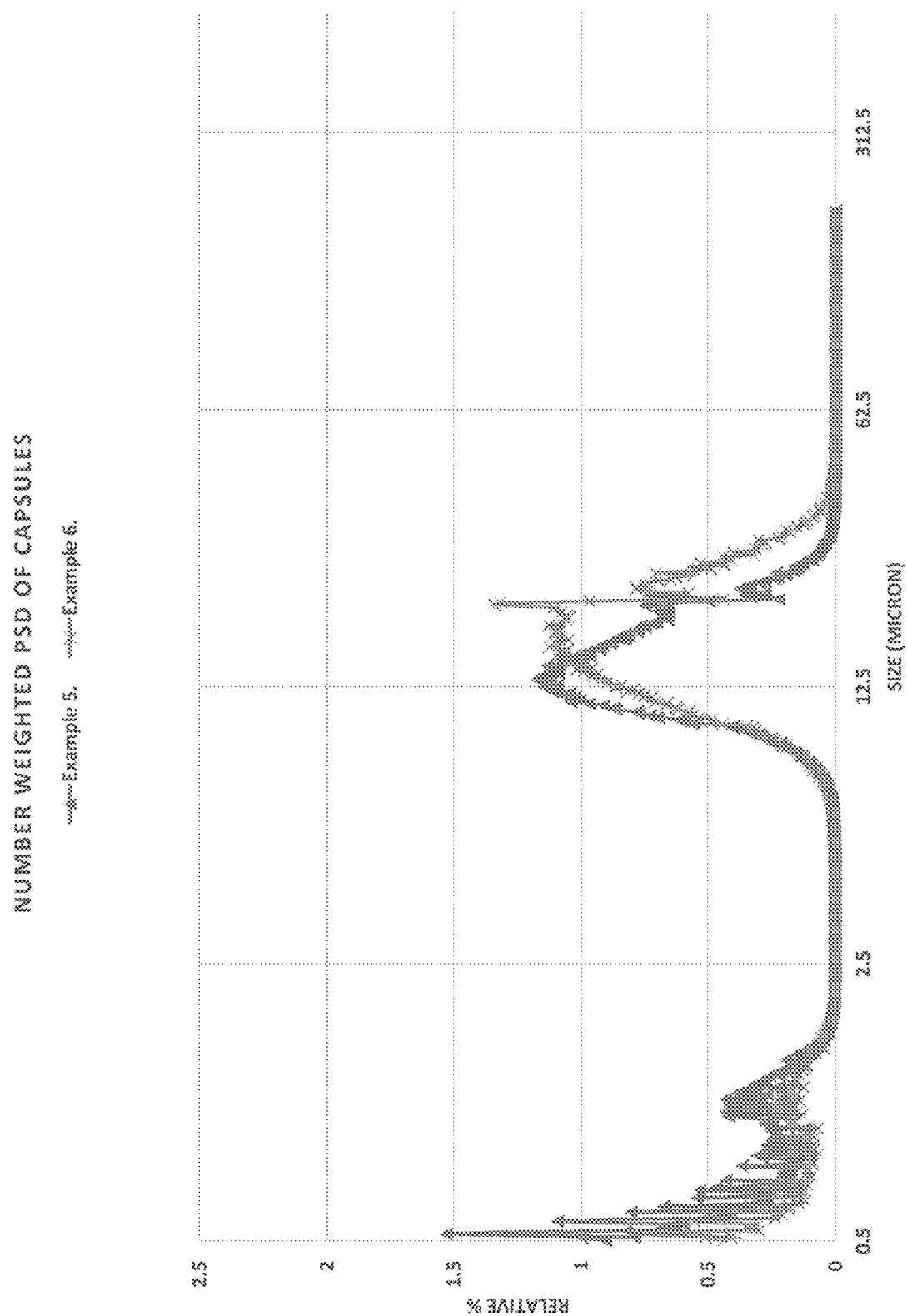
Figure 1D:
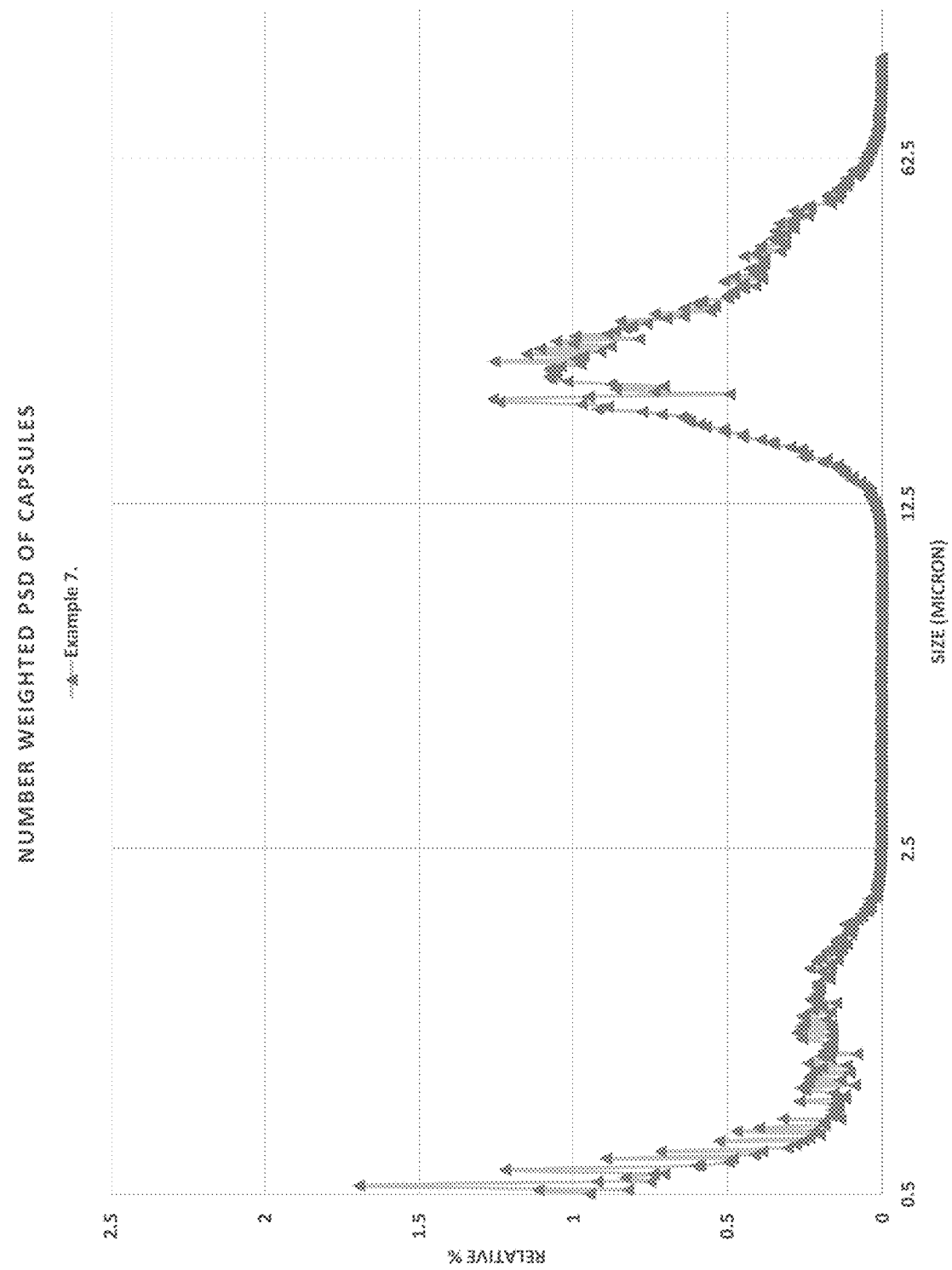

The present invention is a cluster of agglomerated microcapsules comprising two or more microcapsules comprising a core and shell, each microcapsule containing a beneficial core material, preferably which is the same or different; and the shell comprising polymeric wall material surrounding the core and binding the at least two microcapsules forming the cluster. The polymeric wall material of the microcapsule shell can comprise one or more (meth)acrylate polymers and a polyvalent cation.

The cluster of microcapsules may have a number weighted median particle size of the cluster of from 1.1 times to 75 times as compared to the number weighted median particle size of the constituent microcapsules.

A polyvalent cation may be incorporated into the microcapsule shell. The polyvalent cation may be selected from aluminum, zirconium, iron and tin salts. The polyvalent cation may be preferably selected from Al(III), Zr(IV), Sn(IV) and Fe(III).

The shell may also comprise, in addition, from 0.5% to 40% polyvinyl alcohol by weight.

The cluster may have a zeta potential of from −60 millivolts to +60 millivolts or greater, or preferably from −30 millivolts to +30 millivolts. The formation of microcapsule clusters which may be cationic is provided. Cationic microcapsule clusters facilitate adherence to surfaces.

The clusters of microcapsules may have a number weighted median particle size that is at least 1.1 times to 75 times, or preferably at least four times, or more preferably five times, or even more preferably ten times greater than the number weighted median particle size of the microcapsules forming the cluster, or the microcapsules from with the clusters are formed.

The (meth)acrylate polymer wall material of the microcapsule shell may comprise the reaction product of either (A) (a) at least one oil soluble or dispersible amine (meth)acrylate, (b) at least one oil soluble or dispersible acidic (meth)acrylate or at least one oil soluble or dispersible simple acid or both, and (c) at least one oil soluble or dispersible multifunctional (meth)acrylate monomer or oligomer or (B) (a) at least one oil soluble or dispersible acidic (meth)acrylate, (b) at least one oil soluble or dispersible simple base, and (c) at least one oil soluble or dispersible multifunctional (meth)acrylate monomer or oligomer.

Preferably, the cluster of microcapsules may comprise a shell of a (meth)acrylate polymer wherein the (meth)acrylate polymer is the reaction product of (a) at least one oil soluble or dispersible amine (meth)acrylate, (b) at least one oil soluble or dispersible acidic (meth)acrylate or at least one oil soluble or dispersible simple acid or both, and (c) at least one oil soluble or dispersible multifunctional (meth)acrylate monomer or oligomer.

The cluster of microcapsules may comprise a shell of a (meth)acrylate polymer, wherein the (meth)acrylate polymer is the reaction product of (a) at least one oil soluble or dispersible amine (meth)acrylate, (b) at least one oil soluble or dispersible simple acid, and (c) at least one oil soluble or dispersible multifunctional (meth)acrylate monomer or oligomer.

Alternatively, the cluster of microcapsules may comprise a (meth)acrylate polymer, wherein the microcapsule shell comprises in addition melamine resin with the (meth)acrylate polymer and wherein the melamine resin is derived from an aqueous phase and the (meth)acrylate polymer is derived from an oil phase, said (meth)acrylate polymer comprising the reaction product of either (a) at least one oil soluble or dispersible amine (meth)acrylate, (b) at least one oil soluble or dispersible acidic (meth)acrylate or at least one oil soluble or dispersible simple acid or both, and (c) at least one oil soluble or dispersible multifunctional (meth)acrylate monomer or oligomer or (B) (a) at least one oil soluble or dispersible acidic (meth)acrylate, (b) at least one oil soluble or dispersible simple base, and (c) at least one oil soluble or dispersible multifunctional (meth)acrylate monomer or oligomer.

The cluster of microcapsules are substantially reversibly agglomerated. For purposes hereof, "substantially irreversible" means that reversal of clustering is not visually observed following microcapsule formation when the microcapsule slurry composition following manufacture is viewed on a microscope slide, or observed only to an incidental extent such that at least 50% of even at least 75% or even 85% or at least 90%, or even at least 95% of at least 99% by weight of the observed capsules in a representative microscope sampling visually appear clustered, meaning attached to at least one other capsule. Unclustered individual microcapsules in a sample of the slurry account for less than 50% or lees than 25% or less than 10%, or even less that 5%, or less than 1%, or less than 0.1% by weight of the composition.

In one embodiment, a process for preparing a cluster of microcapsules encapsulating an oil phase is provided. The cluster of the invention is able to be irreversibly agglomerated. By irreversible agglomeration is meant that the agglomerates do not readily disperse into single particles when redispersed in water, rather remain as clustered particles. The cluster of microcapsules, when dispersed in aqueous solution, retain a number weighted median particle size of the cluster of rom 1.1 times to 75 times, as compared to the number weighted median particle size of the cluster's constituent microcapsules. The cluster preparation process comprises the following steps: dispersing an oil soluble amine modified polyfunctional polyvinyl monomer or oligomer and an oil soluble bi- or polyfunctional vinyl monomer or oligomer along with a free radical initiator and an organic acid and a core material into an internal phase oil. This is followed by a first heating step comprising, heating for a time and temperature sufficient to pre-polymerize the amine modified polyfunctional polyvinyl monomer or oligomer and oil soluble bi- or polyfunctional vinyl monomer or oligomer. Added to the internal phase oil is a water phase in excess comprising a dispersion in water of a polyacrylic or poly(meth)acrylic acid, a free radical initiator, and an emulsifying agent. The oil phase is emulsified into the water phase forming droplets of the oil phase dispersed in the water phase. The dispersion is heated for a time and temperature sufficient to decompose the free radical initiator in the oil and water phases thereby forming microcapsule wall material at the interface of the water and oil phases, the microcapsules encapsulating the oil phase droplets. A polyvalent cation is added, and heating is continued for a time sufficient to polymerize the wall material and agglomerate the wall material via the polyvalent cation sites incorporated into the microcapsule wall, thereby forming the cluster of microcapsules.

DETAILED DESCRIPTION

It has been found that polyvinyl cations of certain transition metals and post transition metals can selectively aggregate microcapsules by forming irreversible capsule clusters. The effect appears especially with microcapsule walls based on reactive acid or ester groups, and particularly is seen with poly(meth)acrylate type microcapsule wall materials.

The polyvalent cations can include aluminum(III), zirconium(IV), tin(IV), tin (II) and iron(III), but can also include other transition or post transition polyvalent metal cations. Though not being bound be theory, it is believed that polyvalent cations have multiple reactive sites in one molecule to aggregate microcapsules through formation of covalent bonds.

Unlike prior art processes based on addition of deposition aids or charge additive coatings added to capsules or capsule slurries, it has been surprisingly found how to incorporate a polyvalent cation into the microcapsule shell composition. Being bound into the microcapsule wall material, the polyvalent cation is not subject to easy removal. The resultant agglomeration effect is surprisingly not only controllable but observed to be non-reversible and stable.

The composition and process of the invention may be useful with poly(meth)acrylate microcapsules such as described in Schwantes US Publication No. 20060263518. Microcapsules can be produced from an oil soluble amine modified polyfunctional polyvinyl monomer or oligomer and an oil soluble bi- or polyfunctional vinyl monomer or oligomer along with a free radical initiator, such as an azo or peroxy initiator, and an organic acid dispersed into an internal phase oil. This dispersion is heated for a time and temperature sufficient to oligomerize the amine modified polyfunctional poly vinyl monomer and oil soluble bi- or poly functional vinyl monomer or oligomer to form a prepolymer. To this internal phase oil and prepolymer, a water phase is added comprising a dispersion in water of an anionic emulsifier or an initiator. After prereacting and milling, combining of the water phase and oil, a polyvalent cation is added.

The amount of polyvalent cation added is an amount sufficient to effect agglomeration. The polyvalent cation may be at least 0.01% based on the microcapsule weight, or from 0.1% to 14%, preferably from 1% to 12%, more preferably from 1.4% to 9%, even more preferably from 3% to 9%, all on the basis of weight.

Heating is carried out for a time and temperature sufficient to decompose the free radical initiator, which can be placed in one or both of the oil and water phases. The polyvalent cation may be added at the point when wall material starts forming and before the final heating or curing steps to harden the forming polymer shell. "Decompose" the free radical initiator means that the initiator is consumed and, in the process, generates free radicals for furthering propagation of the polymerization reaction of the monomers and oligomers.

In this manner the polyvalent cation is believed to covalently bind at multiple sites of the polyvalent cation to the reactive ester, acid or vinyl linkages of the poly(meth)acrylate polymer.

In forming capsules, milling of the emulsion, before polyvalent cation addition, may be carried out to comminute the emulsion droplets to a particle size of from 0.01 to 100 microns, or even from 0.1 to 100 microns, or even from 0.1 to 10 microns, or even from 0.1 to 8 microns. Often the end use application will dictate the milling size.

The capsules may be prepared according to the process of Linsheng Feng, et al., U.S. Ser. No. 62/064,906 filed Oct. 16, 2014, now U.S. Pat. Nos. 9,714,397 and 9,714,396.

As used herein, reference to the term "(meth)acrylate" or "(meth)acrylic" is to be understood as referring to both the acrylate and the methacrylate versions of the specified monomer, oligomer and/or prepolymer, (for example "alkyl (meth)acrylate" indicates that both alkyl methacrylate and alkyl acrylate are possible, similarly reference to alkyl esters of (meth)acrylic acid indicates that both alkyl esters of acrylic acid and alkyl esters of methacrylic acid are possible, similarly poly(meth)acrylate indicates that both polyacrylate and polymethacrylate are possible). Reference herein to (meth)acrylate or (meth)acrylates, e.g., "water soluble (meth)acrylates", "water phase (meth)acrylate", etc., is intended to cover or include the "(meth)acrylate monomers and/or oligomers." Additionally, the descriptors "water soluble or dispersible", "water soluble", and "water dispersible" when describing (meth)acrylate monomers and/or oligomers or initiators means that the specified component is soluble or dispersible in the given matrix solution on its own or in the presence of a suitable solubilizer or emulsifier or upon attainment of certain temperatures and/or pH.

Poly(meth)acrylate materials are intended to encompass a broad spectrum of polymeric materials including, for example, polyester poly(meth)acrylates, urethane and polyurethane poly(meth)acrylates (especially those prepared by the reaction of an hydroxyalkyl (meth)acrylate with a polyisocyanate or a urethane polyisocyanate), methylcyanoacrylate, ethylcyanoacrylate, diethyleneglycol di(meth)acrylate, trimethylolpropane tri(meth)acrylate, ethylene glycol di(meth)acrylate, allyl (meth)acrylate, glycidyl (meth)acrylate, (meth)acrylate functional silicones, di-, tri- and tetraethylene glycol di(meth)acrylate, dipropylene glycol di(meth)acrylate, polyethylene glycol di(meth)acrylate, di(pentamethylene glycol) di(meth)acrylate, ethylene di(meth)acrylate, neopentyl glycol di(meth)acrylate, trimethylol propane tri(meth)acrylate, ethoxylated bisphenol A di(meth)acrylates, bisphenol A di(meth)acrylates, diglycerol di(meth)acrylate, tetraethylene glycol dichloroacrylate, 1,3-butanediol di(meth)acrylate, neopentyl di(meth)acrylate, trimethylolpropane tri(meth)acrylate, polyethylene glycol di(meth)acrylate and dipropylene glycol di(meth)acrylate and various multifunctional(meth)acrylates.

The cluster of microcapsules may be formed by the steps of:
  (i) forming a first oil phase composition comprising (a) at least one oil soluble or dispersible amine (meth)acrylate, (b) at least one oil soluble or dispersible acidic (meth)acrylate alone or in combination with or at least one oil soluble or dispersible simple acid, (c) at least one oil soluble or dispersible multifunctional (meth) acrylate monomer or oligomer, and, (d) optionally, one or more ingredients or components of core materials intended to be encapsulated;
  (ii) combining and mixing the first oil phase composition with a second oil phase composition comprising a first initiator for effecting polymerization of the (meth) acrylate monomers/oligomers of the first oil phase composition, alone or in combination with the ingredient(s) to be encapsulated, provided that at least one of the first oil phase composition and the second oil phase composition includes at least one of the ingredients or components of core materials to be encapsulated;
  (iii) subjecting the combined oil phase composition to such conditions and for such period of time as is effective for causing the oligomerization/prepolymerization of the (meth)acrylate monomers/oligomers;
  (iv) combining the product of step (iii) with an excess of a first aqueous composition comprising an emulsifier suitable for emulsifying the oil phase composition in water, water, and, optionally, though preferably, either (a) a second initiator, (b) an alkali or alkali salt, or (c) both, and intimately mixing/milling the same to form droplets of the combined oil phase composition dispersed in the first aqueous composition, preferably droplets of a desired or predetermined size;
  (v) applying or subjecting the so formed dispersion to heat or such other conditions as will effect polymerization of the oligomer/prepolymer product of step (iii) at the interface of the oil phase and water phase materials, with or without applying or inducing conditions to cause the reaction product of step (iii) to migrate to said interface, to initiate capsule wall formation at the interface;
  (vi) adding to and mixing with said reaction mix a second aqueous composition comprising water soluble or dispersible (meth)acrylate monomers and/or oligomers, water and, optionally, (a) an emulsifier, preferably a non-ionic emulsifier, (b) a chain transfer agent, (c) a third initiator or (d) a combination of (a) and (b), (a) and (c), (b) and (c) or (a), (b) and (c);
  (vii) subjecting the so formed reaction mix to conditions sufficient to effect deposition and polymerization of the water soluble or dispersible (meth)acrylate monomers and/or oligomers at the interface of the droplet and the aqueous continuous phase concurrent with the continued building of the capsule wall through the polymerization of the oligomer/prepolymer of step (iii);

(viii) adding a polyvalent cation at or following step (vii) or during curing or at the point when the microcapsule wall material starts forming; and (ix) continuing said polymerization process for a sufficient period of time and under such conditions as are necessary to cure and attain the desired microcapsule size and/or capsule wall thickness;

wherein said first initiator comprises at least one initiator capable of effecting oligomerization/prepolymerization of the (meth)acrylate monomers/oligomers of the first oil phase composition, said second initiator comprises at least one water soluble or dispersible initiator, which may be the same as or include, in whole or in part, the first initiator, alone or together with another initiator capable of effecting oligomerization or polymerization of the water soluble or water dispersible acrylate monomers and/or oligomers of the aqueous phase wall forming materials, and said third initiator, if present, comprises at least one at least one water soluble or dispersible initiator capable of effecting polymerization of the water soluble or water dispersible acrylate monomers and/or oligomers.

Alternatively, the cluster of microcapsules may be formed by:

(i) forming a first oil phase composition comprising (a) at least one oil soluble or dispersible acidic (meth)acrylate, (b) at least one oil soluble or dispersible simple base, (c) at least one oil soluble or dispersible multifunctional (meth)acrylate monomer or oligomer, and, (d) optionally, one or more ingredients or components intended to be encapsulated;

(ii) combining and mixing the first oil phase composition with a second oil phase composition comprising the desired one or more ingredients to be encapsulated and, optionally, though preferably, an initiator for effecting polymerization of the (meth)acrylate monomers/oligomers of the first oil phase composition;

(iii) subjecting the combined oil phase composition to such conditions and for such period of time as is effective for causing the oligomerization/prepolymerization of the (meth)acrylate monomers/oligomers;

(iv) combining the oil phase mixture of step (iii) with an excess of a first aqueous composition comprising an emulsifier suitable for emulsifying said oil phase composition in water, water and, optionally, though preferably, (a) a first water soluble initiator, (b) an alkali or alkali salt, or (c) both, and intimately mixing the same to form droplets of the combined oil phase composition dispersed in the first aqueous composition (iii), preferably droplets of a desired or predetermined size;

(v) applying or subjecting the so formed dispersion to heat or such other conditions as will effect polymerization of the oligomer/prepolymer of step (iii) at the interface of the oil phase and water phase materials, with or without applying or inducing conditions to cause the oligomer/prepolymer material to migrate to said interface, to initiate capsule wall formation at the interface;

(vi) adding to and mixing with said reaction mix a second aqueous composition comprising water soluble or dispersible (meth)acrylate monomers and/or oligomers, water and, optionally, (a) an emulsifier, preferably a non-ionic emulsifier, (b) a chain transfer agent, (c) a second water soluble initiator or (d) any or all of the foregoing;

(vii) subjecting the so formed reaction mix to conditions sufficient to effect deposition and polymerization of the water soluble or dispersible (meth)acrylate monomers and/or oligomers at the interface of the droplet and the aqueous matrix concurrent with the continued building of the capsule wall through the polymerization of the oligomer/prepolymer of step (iii);

(viii) adding a polyvalent cation at or following step (vii) or during curing or at the point in the process when the microcapsule wall material starts forming, and (ix) continuing said polymerization process for a sufficient period of time and under such conditions as are necessary to cure and attain the desired microcapsule size and/or capsule wall thickness;

wherein the first water soluble initiator is capable of effecting polymerization of the oil phase oligomer/prepolymer and the water soluble or water dispersible (meth)acrylate and/or the first water soluble initiator is a combination of initiators at least one of which is capable of initiating polymerization of oil phase oligomer/prepolymer and at least one of which is capable of initiating polymerization of the water soluble or water dispersible (meth)acrylate and the second water soluble initiator, which may be the same as, in whole or in part, the first water soluble initiator, comprises at least one initiator capable of initiating polymerization of the water soluble or water dispersible (meth)acrylate. The polyvalent cation is preferably added after the intimate mixing or milling to desired droplet size.

Alternatively, the cluster of microcapsules may be formed by:

(i) forming a first oil phase composition comprising (a) at least one oil soluble or dispersible amine (meth)acrylate, (b) at least one oil soluble or dispersible simple acid, (c) at least one oil soluble or dispersible multifunctional (meth)acrylate monomer or oligomer, and, (d) optionally, one or more ingredients or components of core materials intended to be encapsulated;

(ii) combining and mixing the first oil phase composition with a second oil phase composition comprising the desired one or more ingredients or components of core materials to be encapsulated and, optionally, though preferably, an initiator for effecting polymerization of the (meth)acrylate monomers/oligomers of the first oil phase composition;

(iii) subjecting the combined oil phase composition to such conditions and for such period of time as is effective for causing the oligomerization/prepolymerization of the (meth)acrylate monomers/oligomers;

(iv) combining the oil phase mixture of step (iii) with an excess of a first aqueous composition comprising an emulsifier suitable for emulsifying said oil phase composition in water, water and, optionally, though preferably, (a) a first water soluble initiator, (b) an alkali or alkali salt, or (c) both, and intimately mixing the same to form droplets of the combined oil phase composition dispersed in the first aqueous composition (iii), preferably droplets of a desired or predetermined size;

(v) applying or subjecting the so formed dispersion to heat or such other conditions as will effect polymerization of the oligomer/prepolymer of step (iii) at the interface of the oil phase and water phase materials, with or without applying or inducing conditions to cause the oligomer/prepolymer material to migrate to said interface, to initiate capsule wall formation at the interface;

(vi) adding to and mixing with said reaction mix a second aqueous composition comprising water soluble or dispersible (meth)acrylate monomers and/or oligomers, water and, optionally, (a) an emulsifier, preferably a non-ionic emulsifier, (b) a chain transfer agent, (c) a second water soluble initiator or (d) any or all of the foregoing (vii) subjecting the so formed reaction mix to conditions sufficient to effect deposition and polymerization of the water soluble or dispersible (meth)acrylate monomers and/or oligomers at the interface of the droplet and the aqueous matrix concurrent with the continued building of the capsule wall through the polymerization of the oligomer/prepolymer of step (iii), and (viii) adding a polyvalent cation at or following step (vii) or during curing or at the point in the process when the microcapsule wall starts forming, and (ix) continuing said polymerization process for a sufficient period of time and under such conditions as are necessary to cure and attain the desired microcapsule size and/or capsule wall thickness;

wherein the first water soluble initiator is capable of effecting polymerization of the oil phase oligomer/prepolymer and the water soluble or water dispersible (meth)acrylate and/or the first water soluble initiator is a combination of initiators at least one of which is capable of initiating polymerization of oil phase oligomer/prepolymer and at least one of which is capable of initiating polymerization of the water soluble or water dispersible (meth)acrylate and the second water soluble initiator, which may be the same as, in whole or in part, the first water soluble initiator, comprises at least one initiator capable of initiating polymerization of the water soluble or water dispersible (meth)acrylate.

Alternatively, the cluster of microcapsules may be formed by:

(i) forming a first oil phase composition comprising one or more oil soluble or dispersible mono-, di- or multi-functional (meth)acrylate monomers or oligomers, and, optionally, one or more ingredients or components of core materials intended to be encapsulated;

(ii) combining and mixing the first oil phase composition with a second oil phase composition comprising the desired one or more ingredients or components of core materials to be encapsulated and, optionally, though preferably, an initiator for effecting polymerization of the (meth)acrylate monomers/oligomers of the first oil phase composition;

(iii) subjecting the combined oil phase composition to such conditions and for such period of time as is effective for causing the oligomerization/prepolymerization of the (meth)acrylate monomers/oligomers;

(iv) combining the oil phase mixture of step (iii) with an excess of a first aqueous composition comprising an emulsifier suitable for emulsifying said oil phase composition in water, water and, optionally, though preferably, (a) a first water soluble initiator, (b) an alkali or alkali salt, or (c) both, and intimately mixing the same to form droplets of the combined oil phase composition dispersed in the first aqueous composition (iii), preferably droplets of a desired or predetermined size;

(v) applying or subjecting the so formed dispersion to heat or such other conditions as will effect polymerization of the oligomer/prepolymer of step (iii) at the interface of the oil phase and water phase materials, with or without applying or inducing conditions to cause the oligomer/prepolymer material to migrate to said interface, to initiate capsule wall formation at the interface;

(vi) adding to and mixing with said reaction mix a second aqueous composition comprising water soluble or dispersible (meth)acrylate monomers and/or oligomers, water and, optionally, (a) an emulsifier, preferably a non-ionic emulsifier, (b) a chain transfer agent, (c) a second water soluble initiator or (d) a combination of (a) and (b), (a) and (c), (b) and (c) or (a), (b) and (c);

(vii) subjecting the so formed reaction mix to conditions sufficient to effect deposition and polymerization of the water soluble or dispersible (meth)acrylate monomers and/or oligomers at the interface of the droplet and the aqueous matrix concurrent with the continued building of the capsule wall through the polymerization of the oligomer/prepolymer of step (iii);

(viii) adding a polyvalent cation at or following step (vii) or during curing or when the microcapsule wall starts forming, and (ix) continuing said polymerization process for a sufficient period of time and under such conditions as are necessary to cure and attain the desired microcapsule size and/or capsule wall thickness;

wherein the first water soluble initiator is capable of effecting polymerization of the oil phase oligomer/prepolymer and the water soluble or water dispersible (meth)acrylate and/or the first water soluble initiator is a combination of initiators at least one of which is capable of initiating polymerization of oil phase oligomer/prepolymer and at least one of which is capable of initiating polymerization of the water soluble or water dispersible (meth)acrylate and the second water soluble initiator, which may be the same as, in whole or in part, the first water soluble initiator, comprises at least one initiator capable of effecting polymerization of the water soluble or water dispersible (meth)acrylate.

Alternatively, the cluster of microcapsules may be formed by:

(i) forming an oil phase composition comprising one or more oil soluble or dispersible mono-, di- or multi-functional (meth)acrylate monomers or oligomers, and, optionally, through preferably, an initiator for effecting polymerization of the (meth)acrylate monomers/oligomers, and one or more ingredients or components of core materials intended to be encapsulated;

(ii) combining the oil phase (i) with an excess of a first aqueous composition comprising an emulsifier suitable for emulsifying said oil phase composition in water, water and, optionally, though preferably, (a) a first water soluble initiator, (b) an alkali or alkali salt, or (c) both, and intimately mixing the same to form droplets of the combined oil phase composition dispersed in the first aqueous composition (iii), preferably droplets of a desired or predetermined size;

(iii) applying or subjecting the so formed dispersion to heat or such other conditions as will effect polymerization of the oligomer/prepolymer of step (i) at the interface of the oil phase and water phase materials, with or without applying or inducing conditions to cause the oligomer/prepolymer material to migrate to said interface, to initiate capsule wall formation at the interface;

(iv) adding to and mixing with said reaction mix a second aqueous composition comprising water soluble or dispersible (meth)acrylate monomers and/or oligomers, water and, optionally, (a) an emulsifier, preferably a non-ionic emulsifier, (b) a chain transfer agent, (c) a second water soluble initiator or (d) a combination of (a) and (b), (a) and (c), (b) and (c) or (a), (b) and (c);

(v) subjecting the so formed reaction mix to conditions sufficient to effect deposition and polymerization of the water soluble or dispersible (meth)acrylate monomers and/or oligomers at the interface of the droplet and the aqueous matrix concurrent with the continued building of the capsule wall through the polymerization of the oligomer/prepolymer of step (i);

(vi) adding a polyvalent cation at or following step (v) or during curing or when the microcapsule wall starts forming, and (vii) continuing said polymerization process for a sufficient period of time and under such conditions as are necessary to cure and attain the desired microcapsule size and/or capsule wall thickness;

wherein the first water soluble initiator is capable of effecting polymerization of the oil phase oligomer/prepolymer and the water soluble or water dispersible (meth)acrylate and/or the first water soluble initiator is a combination of initiators at least one of which is capable of initiating polymerization of oil phase oligomer/prepolymer and at least one of which is capable of initiating polymerization of the water soluble or water dispersible (meth)acrylate and the second water soluble initiator, which may be the same as, in whole or in part, the first water soluble initiator, comprises at least one initiator capable of initiating polymerization of the water soluble or water dispersible (meth)acrylate.

In a further aspect, a process of making microcapsules is disclosed, each of said microcapsules independently having a size of from 2 microns to 80 microns, preferably from 5 microns to 50 microns or more preferably from 10 microns to 30 microns, the microcapsules comprising: (a) a core that comprises, based on total microcapsule weight, from 6% to 99.9%, preferably from 11% to 95%, or more preferably from 50% to 75%, of a benefit agent and from 0.1% to 94%, preferably from 5% to 89%, or more preferably from 25% to 50% of an optional partitioning modifier and/or density modifier; and (b) a shell that encapsulates said core, said shell comprising, based on total shell weight, from 50% to 100% by weight, preferably from 70% to 100% or more preferably from 80% to 100% of a polyacrylate and from 0.1 to 30%, or preferably from 1% to 25%, or more preferably from 1 to 14%, or even more preferably from 1.4% to 12.1%, or even much more preferably from 3% to 9% of a polyvalent cation based on the dry weight of polyvalent cation over the total dry weight of microcapsules.

In one aspect, a process of making a microcapsules is disclosed, comprising: a.) reacting a multifunctional acrylate monomer and/or multifunctional acrylate oligomer, in one aspect a multifunctional methacrylate monomer and/or multifunctional methacrylate oligomer, in a benefit agent comprising an optional partitioning modifier and/or density modifier with a composition comprising: i) an amine acrylate and/or methacrylate and a strong acid; or ii) a carboxylic acid acrylate and/or methacrylate monomer and a strong base; or iii) an amine acrylate and/or methacrylate monomer and a carboxylic acid acrylate and/or carboxylic acid methacrylate monomer to form a core composition, b.) forming an emulsion comprising said core composition, and from 0.1 to 30, or preferably from 1% to 25%, or more preferably from 1 to 14%, or even more preferably from 1.4% to 12.1% or even much more preferably from 3% to 9% of a polyvalent cation, and optionally a surfactant, an anionic, cationic or neutral surfactant, and water; c.) curing said emulsion by applying a sufficient amount of thermal, UV, and/or electron beam energy to said emulsion to induce sufficient free-radical polymerization to form a microcapsule having a core comprising said benefit agent and a shell comprising an acrylate, said shell encapsulating said benefit agent.

The properties of the oil can influence the permeability of the polyacrylate shell material established at the oil/water interface. If the oil phase comprises highly polar materials, these materials will reduce the diffusion of the acrylate oligomers and polymers to the oil/water interface and result in a thin, more permeable shell. Incorporation of partitioning modifier as taught in US Publication 20150071977 can influence and be used to adjust the polarity of the core, thereby changing the partition coefficient of the polar materials in the partitioning modifier versus the acrylate oligomers, and can result in the establishment of an impermeable shell.

If desired, a partitioning modifier and/or a density modifier may be combined with core oil material prior to incorporation of the wall forming monomers and addition of polyvalent cation before wall polymerization. A polyvalent cation is incorporated into the polymeric wall of the microcapsule and contributes to cluster formation. Advantageously the microcapsules have low leakage of core material.

Amine (Meth)Acrylates

Amine (meth)acrylates may include, by way of illustration and not limitation, oil soluble or dispersible amine modified (meth)acrylate monomers such as mono or diacrylate amines, mono or dimethacrylate amines, amine modified polyetheracrylates, amine modified polyethermethacrylates, aminoalkyl acrylates, aminoalkyl methacrylates and the like. The amines can include primary, secondary or tertiary amines.

The amine (meth)acrylate can be an aminoalkyl acrylate or aminoalkyl methacrylate including, for example, but not by way of limitation, ethylaminoethyl acrylate, ethylaminoethyl methacrylate, aminoethyl acrylate, aminoethyl methacrylate, tertiarybutyl ethylamino acrylate, tertiarybutyl ethylamino methacrylate, tertiarybutyl aminoethyl acrylate, tertiarybutyl aminoethyl methacrylate, diethylamino acrylate, diethylamino methacrylate, diethylaminoethyl acrylate, diethylaminoethyl methacrylate, dimethylaminoethyl acrylate and dimethylaminoethyl methacrylate. The amine (meth)acrylate can be an aminoethylacrylate or aminoethylmethacrylate, or tertiarybutyl aminoethyl methacrylate.

An oil soluble or dispersible simple base can be employed in place of or in addition to the amine acrylate. The simple base can be a primary, secondary or tertiary amine or amino compound including, for example, aliphatic amines, cycloaliphatic amines, amidoamines and polyamides. Specific exemplary amines include diethylene triamine, triethylenetetraamine and tetraethylenepentaamine, Lewis bases such as o-(diethylaminoethyl)phenol, tris-(dimethylaminomethyl)phenol and 2-ethyl-4-methyl imidazole base; and Schiff bases such as methyl anthranilate/citronellal Schiff base, isononylaldehyde/methylanthranilate Schiff base, methyl N-(3,7-dimethyl-7-hydroxyoctylidene)-anthranilate Schiff-base.

Suitable oil-soluble or dispersible (meth)acrylate acids generally have a carboxy moiety bonded to a carbon atom of a hydrocarbyl group. Exemplary acid (meth)acrylates include carboxymethyl acrylate, 2-carboxyethyl acrylate, 2-carboxypropyl acrylate, 3-carboxypropyl acrylate, 4-carboxybutyl acrylate, carboxymethyl methacrylate, 2-carboxyethyl methacrylate, 2-carboxypropyl methacrylate, 3-carboxypropyl methacrylate, 4-carboxybutyl methacrylate, and the like.

Where an oil soluble or dispersible simple acid is employed in place of or in addition to the acid (meth)acrylate, the oil soluble acid may be preferably an organic acid. The organic acid can be selected from various acids such as carboxy acids, monoalkyl maleates such as monomethyl-, monoethyl- or monobutyl-maleate. Other useful organic acids include beta-carboxyethyl acrylate, organic sulfonic acids such as alkyl benzene sulfonic acid, linear alkyl benzene sulfonic acid, tridecylbenzene sulfonic acid, linear trialkylbenzene sulfonic acid such as linear tridecylbenzene sulfonic acid, alkyldiphenyloxide sulfonic acid, dodecyl diphenyloxide disulfonic acid, branched C12 diphenyloxide disulfonic acid, alkylbenzene sulfonic acid, dodecyl benzene sulfonic acid, dialkylnaphthalene disulfonic acid, such as dinonylnaphthalene disulfonic acid, 4-hydrozino benzene sulfonic acid, acrylic acid, methacrylic acid, and the like. The organic acid typically is selected to be dispersible in the oil phase and sparingly soluble in the water phase.

Multifunctional (Meth)Acrylates

The oil-soluble or dispersible multifunctional (meth)acrylate monomers and oligomers may contain more than one polymerizable group or double bond, such as two or more acrylate or methacrylate groups or other functional groups. Suitable monomers and oligomers may include, by way of illustration and not limitation, allyl methacrylate; triethylene glycol dimethacrylate; ethylene glycol dimethacrylate; diethylene glycol dimethacrylate; aliphatic or aromatic urethane acrylates, such as hexa-functional aromatic urethane acrylates; ethoxylated aliphatic difunctional urethane methacrylates; aliphatic or aromatic urethane methacrylates, such as tetra-functional aromatic methacrylates; epoxy acrylates; epoxymethacrylates; tetraethylene glycol dimethacrylate; polyethylene glycol dimethacrylate; 1,3 butanediol diacrylate; 1,4-butanediol dimethacrylate; 1,4-butanediol diacrylate; diethylene glycol diacrylate; 1.6 hexanediol diacrylate; 1,6 hexanediol dimethacrylate; neopentyl glycol diacrylate; polyethylene glycol diacrylate; tetraethylene glycol diacrylate; triethylene glycol diacrylate; 1,3 butylene glycol dimethacrylate; tripropylene glycol diacrylate; ethoxylated bisphenol A diacrylate; ethoxylated bisphenol A dimethylacrylate; dipropylene glycol diacrylate; alkoxylated hexanediol diacrylate; alkoxylated cyclohexane dimethanol diacrylate; propoxylated neopentyl glycol diacrylate; trimethylolpropane trimethacrylate; trimethylolpropane triacrylate: pentaerythritol triacrylate; pentaerythritol tetramethacrylate; ethoxylated trimethylolpropane triacrylate; propoxylated trimethylolpropane triacrylate; propoxylated glyceryl triacrylate; ditrimethylolpropane tetraacrylate; dipentaerythritol pentaacrylate; ethoxylated pentaerythritol tetraacrylate; bis-phenol A diacrylate; bis-phenol A dimethacrylate, hexa-functional aromatic urethane acrylate; hexa-functional aromatic urethane methacrylate; and the like.

The constituents in the oil phase or phases by weight may be from 0.1 to 15%, or preferably from 0.2 to 10%, or more preferably from 0.4 to 5% by weight of amine (meth)acrylate and/or simple base; from 0.1 to 15%, preferably from 0.2 to 10%, or more preferably from 0.4 to 5% by weight of acid (meth)acrylate and/or simple acid; and from 99.8 to 60%, or preferably from 99.8 to 70%, or more preferably from 99.6 to 80%, even more preferably from 99.2 to 90% of multifunctional (meth)acrylate.

Alternatively, when a simple base or simple acid is used, it may be employed in a mole ratio of from 5:1 to 1:5, preferably 3:1 to 1:3, of the acid to amine (meth)acrylate or of the base to acid (meth)acrylate. The oil phase generally may comprise 1-70%, or preferably from 1 to 80% or more preferably from 5-50%, and even more preferably from 10-30% by weight of one or more mono-, bi- or multi-functional oil soluble or dispersible (meth)acrylate monomers and/or oligomers comprising 0-100%, or preferably 5-70%, by weight of one or more oil soluble mono-functional acrylate monomers; and/or 0-40% weight of another, copolymerizable mono-functional monomer; and/or 0.1-100%, preferably 10-90%, by weight of one or more bi or multi-functional acrylate monomers/oligomers. Oil soluble mono-acrylates and copolymerizable other mono-functional monomers optionally can be included as well.

Core Materials

The capsules may be useful with a wide variety of capsule contents ("core material") including, by way of illustration and without limitation, various benefit agents, various actives, oils, phase change materials with or without organic or inorganic nucleating agents, alkane waxes, polyethylene waxes, scents, fertilizers, nutrients, herbicides dyes, perfumes, essential oils, fragrances, cleaning oils, polishing oils, flavorants, nutrients, sweeteners, chromogens, pharmaceuticals, fertilizers, biological actives, scents, flavorants, sweeteners, fats, pigments, cleaning oils, pharmaceuticals, pharmaceuticals, mold inhibitors, antimicrobial agents, lubricants, biocides, adhesives, curatives by way of illustration and without limitation.

The microcapsule core materials can include materials which alter rheology or flow characteristics, or extend shelf life or product stability. Essential oils as core materials can include, for example, by way of illustration wintergreen oil, cinnamon oil, clove oil, lemon oil, lime oil, orange oil, peppermint oil and the like. Dyes can include fluorans, lactones, indolyl red, I6B, leuco dyes, all by way of illustration and not limitation. The core material should be dispersible or sufficiently soluble in the capsule internal phase material namely in the internal phase oil or soluble or dispersible in the monomers or oligomers solubilized or dispersed in the internal phase oil. The core materials are preferably liquid but can be solid depending on the materials selected, and with temperatures appropriately adjusted to effect dispersion.

With cores that are solid at ambient temperatures, the wall material can usefully enwrap less than the entire core for certain applications where availability of, for example, of an agglomerate core is desired in an application. Such uses can include scent release, cleaning compositions, emollients, cosmetic delivery, fabric treatment, surface modification, actives delivery and the like. Where the microcapsule core material is phase change material, uses can include such encapsulated materials in mattresses, pillows, bedding, textiles, sporting equipment, medical devices, building products, construction products, heating or cooling systems, renewable energy, clothing, athletic surfaces, electronics, automotive, aviation, shoes, beauty care, laundry, and solar energy.

Typically, the core material may be dispersed in an oil phase or phases. At least one of the first oil phase composition, and if a second oil phase composition is used, at least one of the oil phase compositions or each, can contain or have dispersed therein one or more ingredients that are intended to be encapsulated. Reverse water in oil systems are also known.

The core material can be a minor or major constituent of the material encapsulated by the microcapsules. If the core material can function as the oil solvent in the capsules, it is possible to make the core material the major or total material encapsulated. Usually however, the core material is from 0.01 to 99 weight percent of the capsule internal contents, preferably 0.01 to 65 by weight of the capsule internal contents, and more preferably from 0.1 to 45% by weight of the capsule internal contents. With certain applications, the core material can be effective even at just trace quantities.

Oil Phase Carriers and Solvents

Where the core material is not itself sufficient to serve as the oil phase or solvent, the oil phase will further include a suitable carrier and/or solvent. These carriers or solvents preferably have a boiling point greater than 100° C. and low volatility and are non-flammable. Though not limited thereto, the carriers or solvents may preferably comprise one or more esters, preferably with chain lengths of up to 18 carbon atoms or even up to 42 carbon atoms and/or triglycerides such as the esters of C6 to C12 fatty acids and glycerol. Exemplary carriers and solvents include, but are not limited to: ethyldiphenylmethane; butyl biphenyl ethane; benzylxylene; alkyl biphenyls such as propylbiphenyl and butylbiphenyl; dialkyl phthalates e.g. dibutyl phthalate, dioctylphthalate, dinonyl phthalate and ditridecylphthalate; 2,2,4-trimethyl-1,3-pentanediol diisobutyrate; alkyl benzenes such as dodecyl benzene; alkyl or aralkyl benzoates such as benzyl benzoate; diaryl ethers; di(aralkyl)ethers and aryl aralkyl ethers; ethers such as diphenyl ether, dibenzyl ether and phenyl benzyl ether; liquid higher alkyl ketones (having at least 9 carbon atoms); alkyl or aralky benzoates, e.g., benzyl benzoate; alkylated naphthalenes such as dipropylnaphthalene; partially hydrogenated terphenyls; high-boiling straight or branched chain hydrocarbons; alkaryl hydrocarbons such as toluene; vegetable oils such as canola oil, soybean oil, corn oil, sunflower oil, or cottonseed oil; methyl esters of fatty acids derived from transesterification of canola oil, soybean oil, cottonseed oil, corn oil, sunflower oil, pine oil, lemon oil, and olive oil; methyl ester of oleic acid; vegetable oils; esters of vegetable oils, e.g. soybean methyl ester; straight chain saturated paraffinic aliphatic hydrocarbons of from 8 to 24 carbons, alkane waxes, polyethylene waxes, and the like. Mixtures of the above can also be employed. Common diluents such as straight chain hydrocarbons can also be blended with the solvents, or blend of solvents. The solvent is selected on the basis of hydrophobicity and their ability to disperse or solvate the amine (meth)acrylate, the acidic (meth)acrylate, and the multifunctional (meth)acrylate monomer and/or oligomer and/or the acrylate oligomer/prepolymer formed therefrom.

Water Phase

Like the oil phase, the water phase, which forms the continuous phase of the reaction mix for the microencapsulation process, preferably can comprise one composition, or even two distinct compositions which can be combined in the course of the microencapsulation process. In a two water phase process, a first water phase composition can comprise water, an emulsifier, preferably a non-ionic emulsifier, and, optionally, though preferably, at least one initiator and/or an alkali or alkali salt. The second, a second water phase composition, can comprise water, at least water soluble or water dispersible (meth)acrylate monomers and/or oligomers, and, optionally, (a) an emulsifier, preferably a non-ionic emulsifier, (b) a chain transfer agent, (c) a second water phase initiator or (d) (a) and (b), (a) and (c), (b) and (c) or (a), (b) and (c).

Water Phase Acrylates

Where a second water phase composition is used, the second water phase composition comprises one or more water soluble or dispersible (meth)acrylate monomers and/or oligomers. The second water phase generally comprises 0.5-100%, preferably 5-70%, and more preferably 10-50% one or more mono-, bi- or multi-functional water soluble or dispersible (meth)acrylate monomers and/or oligomers. Those skilled in the art will readily recognize and appreciate that many of the acrylate monomers and oligomers disclosed above for use in the oil phase will have some water solubility or water dispersibility, particularly in the presence of a suitable emulsifier, and may be used in the second water phase composition. Similarly, they will recognize and appreciate other acrylic esters that possess water solubility, even low water solubility, and/or water dispersibility. Generally speaking such water soluble or water dispersible (meth) acrylates contain at least one acrylate or methacrylate group and comprise a hydrocarbon portion that is small such that the ester functional group is enough to impart sufficient hydrophilicity to the monomer, as is the case with, for example, 1,3-butanediol diacrylate. Otherwise, the hydrophobicity of the larger hydrocarbon portion of larger acrylate esters may be overcome by the presence of additional functional groups such as amines, urethanes, alcohols or ethers or combinations thereof which enhance the hydrophilicity. Exemplary water soluble or dispersible acrylates or methacrylates include amine modified polyether (meth)acrylate oligomers, hexafunctional aromatic urethane (meth) acrylate oligomers, hydroxyethyl (meth)acrylate, hydroxypropyl (meth)acrylate, methyl methacrylate, butanediol di(meth)acrylate, hexanediol di(meth)acrylate, ethoxylated bisphenol-A diacrylate, ethoxylated bisphenol-A dimethacrylate, isobornyl (meth)acrylate, pentaerythritol tri(meth) acrylate, pentaerythritol tetra(meth)acrylate, penta(meth) acrylate ester, diethylene glycol di(meth)acrylate, dipropylene glycol di(meth)acrylate, triethylene glycol di(meth)acrylate, tripropylene glycol di(meth)acrylate, neopentyl glycol di(meth)acrylate, trimethylolpropane tri(meth) acrylate, methoxy polyethylene glycol mono(meth)acrylate, ethoxylated trimethylolpropane tri(meth)acrylate, and ethoxylated pentaerythritol tetra(meth)acrylate, difunctional aliphatic epoxy (meth)acrylates, polyethylene glycol di(meth)acrylate, polypropylene glycol di(meth)acrylate, alkoxylated mono- or multi-functional (meth)acrylate ester, polyester (meth)acrylate oligomers, amine modified polyether (meth)acrylate oligomers and the like. Especially preferred water soluble or water dispersible (meth)acrylates are the polyethylene glycol di(meth)acrylates, ethoxylated mono- or multi-functional (meth)acrylates, and (meth)acrylate monomers and/or oligomers that are capable of being dispersed in water with a small amount of a suitable emulsifier.

Emulsifier

Optionally, the first water phase composition may contain an emulsifier to aid in the creation of the dispersion of the oil phase in the continuous water phase. Less critical, but again, preferably, the second water phase may also contain an emulsifier, preferably a non-ionic emulsifier, to aid in the dispersion and/or solubility of the water soluble or dispersible acrylate monomer or oligomer in the second water phase.

Emulsifiers of all types are suitable for use in the practice of the present invention though it is to be appreciated, and those skilled in the art will readily recognize that different systems, i.e., oil phase compositions, will be better suited with one or more classes of emulsifiers than others. Specifically, while the present teachings are applicable to anionic, cationic, non-ionic and amphoteric emulsifiers generally, preferred emulsifiers are the cationic and non-ionic emulsifiers, particularly those having polyalkylether units, especially polyethylene oxide units, with degrees of polymerization of the alkylene ether unit of greater than 6. Preferred emulsifiers are those which significantly reduce the interfacial tension between the aqueous phase and dispersed phase, and thereby reduce the tendency for droplet coalescence. In this regard, generally the emulsifiers for use in the first water phase for aiding in the oil in water emulsion or dispersion will have HLB values of from 11 to 17. While emulsifiers of the same HLB value may also be used in a second water phase, those emulsifiers that are used to enhance the solubility and/or dispersibility of the water phase (meth)acrylate in for example a second water phase will generally have HLB values of 16 to 20.

Exemplary useful anionic surfactants and classes of anionic surfactants include: sulfonates; sulfates; sulfosuccinates; sarcosinates; alcohol sulfates; alcohol ether sulfates; alkylaryl ether sulfates; alkylaryl sulfonates such as alkylbenzene sulfonates and alkylnaphthalene sulfonates and salts thereof; alkyl sulfonates; mono- or di-phosphate esters of polyalkoxylated alkyl alcohols or alkylphenols; mono- or di-sulfosuccinate esters of C12 to C15 alkanols or polyalkoxylated C12 to C15 alkanols; ether carboxylates, especially alcohol ether carboxylates; phenolic ether carboxylates; polybasic acid esters of ethoxylated polyoxyalkylene glycols consisting of oxybutylene or the residue of tetrahydrofuran; sulfoalkylamides and salts thereof such as N-methyl-N-oleoyltaurate Na salt; polyoxyalkylene alkylphenol carboxylates; polyoxyalkylene alcohol carboxylates alkyl polyglycoside/alkenyl succinic anhydride condensation products; alkyl ester sulfates; naphthalene sulfonates; naphthalene formaldehyde condensates; alkyl sulfonamides; sulfonated aliphatic polyesters; sulfate esters of styrylphenyl alkoxylates; and sulfonate esters of styrylphenyl alkoxylates and their corresponding sodium, potassium, calcium, magnesium, zinc, ammonium, alkylammonium, diethanolammonium, or triethanolammonium salts; salts of ligninsulfonic acid such as the sodium, potassium, magnesium, calcium or ammonium salt; polyarylphenol polyalkoxyether sulfates and polyarylphenol polyalkoxyether phosphates; and sulfated alkyl phenol ethoxylates and phosphated alkyl phenol ethoxylates; sodium lauryl sulfate; sodium laureth sulfate; ammonium lauryl sulfate; ammonium laureth sulfate; sodium methyl cocoyl taurate; sodium lauroyl sarcosinate; sodium cocoyl sarcosinate; potassium coco hydrolyzed collagen; TEA (triethanolamine) lauryl sulfate; TEA (Triethanolamine) laureth sulfate; lauryl or cocoyl sarcosine; disodium oleamide sulfosuccinate; disodium laureth sulfosuccinate; disodium dioctyl sulfosuccinate; N-methyl-N-oleoyltaurate Na salt; tristyrylphenol sulphate; ethoxylated lignin sulfonate; ethoxylated nonylphenol phosphate ester; calcium alkylbenzene sulfonate; ethoxylated tridecylalcohol phosphate ester, dialkyl sulfosuccinates; perfluoro (C5-C18)alkyl phosphonic acids; perfluoro(C6-C18)alkyl-phosphinic acids; perfluoro(C3-C20)alkyl esters of carboxylic acids; alkenyl succinic acid diglucamides; alkenyl succinic acid alkoxylates; sodium dialkyl sulfosuccinates; and alkenyl succinic acid alkylpolyglycosides. Further exemplification of suitable anionic emulsifiers include, but are not limited to, water-soluble salts of alkyl sulfates, alkyl ether sulfates, alkyl isothionates, alkyl carboxylates, alkyl sulfosuccinates, alkyl succinamates, alkyl sulfate salts such as sodium dodecyl sulfate, alkyl sarcosinates, alkyl derivatives of protein hydrolysates, acyl aspartates, alkyl or alkyl ether or alkylaryl ether phosphate esters, sodium dodecyl sulphate, phospholipids or lecithin, or soaps, sodium, potassium or ammonium stearate, oleate or palmitate, alkylarylsufonic acid salts such as sodium dodecylbenzenesulfonate, sodium dialkylsulfosuccinates, dioctyl sulfosuccinate, sodium dilaurylsulfosuccinate, poly(styrene sulfonate) sodium salt, alkylene-maleic anhydride copolymers such as isobutylene-maleic anhydride copolymer, or ethylene maleic anhydride copolymer gum arabic, sodium alginate, carboxymethylcellulose, cellulose sulfate and pectin, poly(styrene sulfonate), pectic acid, tragacanth gum, almond gum and agar; semi-synthetic polymers such as carboxymethyl cellulose, sulfated cellulose, sulfated methylcellulose, carboxymethyl starch, phosphated starch, lignin sulfonic acid; maleic anhydride copolymers (including hydrolysates thereof), polyacrylic acid, polymethacrylic acid, acrylic acid alkyl acrylate copolymers such as acrylic acid butyl acrylate copolymer or crotonic acid homopolymers and copolymers, vinylbenzenesulfonic acid or 2-acrylamido-2-methylpropanesulfonic acid homopolymers and copolymers, and partial amide or partial ester of such polymers and copolymers, carboxymodified polyvinyl alcohol, sulfonic acid-modified polyvinyl alcohol and phosphoric acid-modified polyvinyl alcohol, phosphated or sulfated tristyrylphenol ethoxylates.

Useful amphoteric and cationic emulsifiers include alkylpolyglycosides; betaines; sulfobetaines; glycinates; alkanol amides of C8 to C18 fatty acids and C8 to C18 fatty amine polyalkoxylates; C10 to C18 alkyldimethylbenzylammonium chlorides; coconut alkyldimethylaminoacetic acids; phosphate esters of C8 to C18 a fatty amine polyalkoxylates; alkylpolyglycosides (APG) obtainable from an acid-catalyzed Fischer reaction of starch or glucose syrups with fatty alcohols, in particular C8 to C18 alcohols, especially the C8 to C10 and C12 to C14 alkylpolyglycosides having a degree of polymerization of 1.3 to 1.6, in particular 1.4 or 1.5. Additional cationic emulsifiers include quaternary ammonium compounds with a long-chain aliphatic radical, e.g. distearyldiammonium chloride, and fatty amines. Among the cationic emulsifiers which may be mentioned are alkyldimethylbenzylammonium halides, alkyldimethylethyl ammonium halides, etc. specific cationic emulsifiers include palmitamidopropyl trimonium chloride, distearyl dimonium chloride, cetyltrimethylammonium chloride, and polyethyleneimine. Additional amphoteric emulsifiers include alkylaminoalkane carboxylic acids betaines, sulphobetaines, imidazoline derivatives, lauroamphoglycinate, sodium cocoaminopropionate, and the zwitterionic emulsifier cocoamidopropyl betaine.

Useful non-ionic emulsifiers typically have at least one non-ionic hydrophilic functional group. Preferred non-ionic hydrophilic functional groups are alcohols and amides and combinations thereof. Examples of non-ionic emulsifiers include: mono and diglycerides; polyarylphenol polyethoxy ethers; polyalkylphenol polyethoxy ethers; polyglycol ether derivatives of saturated fatty acids; polyglycol ether derivatives of unsaturated fatty acids; polyglycol ether derivatives of aliphatic alcohols; polyglycol ether derivatives of cycloaliphatic alcohols; fatty acid esters of polyoxyethylene sorbitan; alkoxylated vegetable oils; alkoxylated acetylenic diols; polyalkoxylated alkylphenols; fatty acid alkoxylates; sorbitan alkoxylates; sorbitol esters; C8 to C22 alkyl or alkenyl polyglycosides; polyalkoxy styrylaryl ethers; amine oxides especially alkylamine oxides; block copolymer ethers; polyalkoxylated fatty glyceride; polyalkylene glycol ethers; linear aliphatic or aromatic polyesters; organo silicones; polyaryl phenols; sorbitol ester alkoxylates; and mono- and diesters of ethylene glycol and mixtures thereof; ethoxylated tristyrylphenol; ethoxylated fatty alcohol; ethoxylated lauryl alcohol; ethoxylated castor oil; and ethoxylated nonylphenol; alkoxylated alcohols, amines or acids; amides of fatty acids such as stearamide, lauramide diethanolamide, and lauramide monoethanolamide; long chain fatty alcohols such as cetyl alcohol and stearyl alcohol; glycerol esters such as glyceryl laurate; polyoxyalkylene glycols and alkyl and aryl ethers of polyoxyalkylene glycols such as polyoxyethylene glycol nonylphenyl ether and polypropylene glycol stearyl ether. Polyethylene glycol oligomers and alkyl or aryl ethers or esters of oligomeric polyethylene glycol are preferred. Also preferred as nonionic emulsifiers are polyvinyl alcohol, polyvinyl acetate, copolymers of polyvinyl alcohol and polyvinylacetate, carboxylated or partially hydrolyzed polyvinyl alcohol, methyl cellulose, various latex materials, stearates, lecithins, and various surfactants. It is known that polyvinyl alcohol is typically prepared by the partial or complete hydrolysis of polyvinyl acetate. Accordingly, by reference to polyvinyl alcohol we intend to include both completely and partially hydrolyzed polyvinyl acetate. With respect to the latter, it is preferred that the polyvinyl acetate be at least 50 mole % hydrolyzed, more preferably, at least 75 mole % hydrolyzed.

Where the emulsifier is a polymeric emulsifier, especially one having or derived from an acrylic ester, e.g., a polyacrylate or methacrylate, the molecular weight may be generally at least 10,000, preferably at least 20,000, most preferably 30,000 or more. Additionally, the amount of emulsifier is typically from 0.1 to 40% by weight, more preferably from 0.2 to 15 percent, most preferably from 0.5 to 10 percent by weight based on the total weight of the formulation. It is to be appreciated that certain acrylic polymers and copolymers may perform both as an emulsifier as well as a polymerizable and/or non-polymerizable component in forming the microcapsule wall. With respect to the latter, the polymeric emulsifier, particularly those in the nature of higher molecular weight polymers, are trapped and/or incorporated into the polymer wall or walls as formed. This is especially likely where the nature of a particular phase changes and the solubilized polymer comes out of solution.

Chain Transfer Agents

Optionally, though preferably, the water phase, particularly the second water phase composition further includes at least one chain transfer agents include, for example, lower alkyl alcohols having from 1 to 5 carbon atoms, mercaptoethanol, mercaptopropanol, thioglycolic acid, isooctylmercaptoproprionate, tert-nonylmercaptan, pentaerythritol tetrakis(3-mercaptoproprionate), dodecylmercaptan, formic acid, halogenated hydrocarbons, such as bromoethane, bromotrichloromethane, or carbon tetrachloride, and the sulfate, bisulfate, hydrosulfate, phosphate, monohydrogen phosphate, dihydrogen phosphate, toluene sulfonate, and benzoate salts of sodium and potassium, especially sodium hypophosphite and sodium bisulfate. If present the chain transfer agents are preferably used in amounts ranging from 0.01 to 5%, more preferably from 0.5 to 3% by weight with respect to the monomers and/or oligomers employed.

Initiators

Suitable initiators for effecting polymerization of the various (meth)acrylate monomer, oligomers and/or prepolymers may be added to or present in both the oil phase and the water phase compositions. Preferably, an initiator may be present in the second oil phase composition, which is free of the aforementioned oil phase (meth)acrylate monomers, oligomers and prepolymers. Similarly, at least one initiator may be also present in the first water phase, which is free of the aforementioned water soluble or water dispersible (meth)acrylate monomers and/or oligomers. In both instances it may be desirable to add the initiator to the (meth)acrylate-free compositions so as to avoid unwanted or unintended polymerization. By keeping the two separate, one has better control over when polymerization is to begin, particularly in processes, like the instant, where conditions may give rise to activation of the initiator before desired.

Selection of the initiator is dependent, in part, upon the monomers, oligomers and/or prepolymers to be polymerized or further oligomerized, the method by which the initiator is activated, and whether the initiator is to be present in the oil phase or the water phase. Generally speaking, the preferred initiators are energy activated free radical initiators meaning that they generate free radicals when subjected to heat or other energy input. Preferred free radical initiators include peroxy initiators, azo initiators, peroxides, and compounds such as 2,2'-azobismethylbutyronitrile, dibenzoyl peroxide. More particularly, and without limitation the free radical initiator can be selected from the group of initiators comprising an azo or peroxy initiator, such as peroxide, dialkyl peroxide, alkyl peroxide, peroxyester, peroxycarbonate, peroxyketone and peroxydicarbonate, 2,2'-azobis (isobutylnitrile), 2,2'-azobis(2,4-dimethylpentane-nitrile), 2,2-azobis (2,4-dimethylvaleronitrile), 2,2'-azobis(2-methylpropanenitrile), 2,2'-azobis (methylbutyronitrile), 1,1'-azobis (cyclohexanecarbonitrile), 1,1'-azobis(cyano-cyclohexane), benzoyl peroxide, decanoyl peroxide; lauroyl peroxide; benzoyl peroxide, di(n-propyl) peroxydicarbonate, di(sec-butyl) peroxydicarbonate, di(2-ethylhexyl) peroxydicarbonate, 1,1-dimethyl-3-hydroxybutyl peroxyneodecanoate, .alpha.-cumyl peroxyneoheptanoate, t-amyl peroxyneodecanoate, t-butyl peroxyneodecanoate, t-amyl peroxypivalate, t-butyl peroxypivalate, 2,5-dimethyl 2,5-di(2-ethylhexanoyl peroxy) hexane, t-amyl peroxy-2-ethyl-hexanoate, t-butyl peroxy-2-ethylhexanoate, t-butyl peroxyacetate, di-t-amyl peroxyacetate, t-butyl peroxide, di-t-amyl peroxide, 2,5-dimethyl-2, 5-di-(t-butylperoxy)hexyne-3, cumene hydroperoxide, 1,1-di-(t-butylperoxy)-3,3,5-trimethyl-cyclohexane, 1,1-di-(t-butylperoxy)-cyclohexane, 1,1-di-(t-amylperoxy)-cyclohexane, ethyl-3,3-di-(t-butylperoxy)-butyrate, t-amyl perbenzoate, t-butyl perbenzoate, ethyl 3,3-di-(t-amylperoxy)-butyrate, and the like.

Useful water soluble initiators include persulfate salts, such as ammonium persulfate, sodium persulfate and potassium persulfate; peroxides, such as hydrogen peroxide, oxalic acid peroxide, acetic acid peroxide and succinic acid peroxide; and various azo compounds.

Actinic radiation activated initiators can also optionally be employed. Suitable actinic radiation activated initiators include those activated by UV light, IR radiation, visible light, electron beam and the like. Actinic radiation activated initiators can be used in place of, in whole or in part, heat activated initiators. For example, it may be desirable to use heat initiators for one or more polymerization steps and an actinic radiation activated initiator for one or more other polymerization steps.

Preferred actinic radiation activated initiators may be the UV initiators. Exemplary UV initiators include benzophenone; acetophenone; benzil; benzaldehyde; o-chlorobenzaldehyde; xanthone; thioxanthone; 9,10-anthraquinone; 1-hydroxycyclohexyl phenyl ketone; 2,2-diethoxyacetophenone; dimethoxyphenylacetophenone; methyl diethanolamine; dimethylaminobenzoate; 2-hydroxy-2-methyl-1-phenylpropane-1-one; 2,2-di-sec-butoxyacetophenone; 2,2-dimethoxy-1,2-diphenylethan-1-one; dimethoxyketal; phenyl glyoxal 2,2'-diethoxyacetophenone; hydroxycyclohexyl phenyl ketone; alpha-hydroxyketones; alpha-amino-ketones; alpha and beta naphthyl carbonyl compounds; benzoin ethers such as benzoin methyl ether; benzil; benzil ketals such as benzil dimethyl ketal; acetophenone; fluorenone; 2-hydroxy-2-methyl-1-phenylpropan-1-one, and the like. UV initiators of this kind are available commercially, e.g., Irgacure™ 184 or Degacure™ 1173 from Ciba. Thermal initiators are available from DuPont.

Actinic radiation activated initiators, preferably UV initiators, can be employed in addition to and/or as an alternative to heat activated initiators. The presence of both a heat activated initiator and actinic radiation activated and initiator results in a dual cure system or one that provides an optional thermal or optional light or optional UV initiated cure method. Given the selectivity of certain initiators for polymerizing certain monomers, oligomers and/or prepolymers, one can tailor their encapsulation process to effect polymerization in only one phase as opposed to multiple phases and/or polymerization of one or more monomers but less than all free radically curable or polymerizable monomers. Furthermore, given the half-lives of certain of the free radical initiators, better control can be achieved of the extent or degree of polymerization so as to prevent premature curing in the encapsulation process. Different temperatures for different polymerization steps can be tailored to regulate the rate of polymerization, again to better control the formation of the capsule wall and its constituents. For example, in preparing the oil phase oligomer/prepolymer one may use a heat activated initiator at one temperature and the same or a different initiator at a higher temperature to achieve the further polymerization thereof in forming the capsule wall. Additionally, it is possible to employ three different polymerization temperatures in the encapsulation process where the first, preferably the lower temperature, is employed to prepare the oil phase (meth)acrylate oligomer/prepolymer. A second higher temperature may be employed to initiate wall formation through polymerization of the oil phase (meth) acrylate oligomer/prepolymer or of the water soluble or water dispersible (meth)acrylate monomers and/or oligomers, or both. And, a final, yet higher still, temperature to fully cure or polymerize the capsule wall material. Again, as noted, one may substitute a non-heat activated initiator for the heat activated initiator in any one or more of these polymerization steps and/or add a non-heat activated initiator which is specific for said one or more of the foregoing polymerization steps.

For specialized microencapsulation processes, the use of initiators, e.g., thioxanthones, phosphine oxides, metallocenes, tertiary aminobenzenes or tertiary aminobenzophenones, which break down into free radicals on exposure to visible light may be effectively used. Such microencapsulation systems however typically require special handling of the system to prevent premature polymerization or oligomerization by appropriate control of lighting conditions.

In general, the initiator will be present in an amount of 0.01 to 10.0 weight percent, preferably 0.1 to 6 weight percent, more preferably 0.5 to 2.5 weight percent, in any of the water or oil phases, based on the total weight of all constituents. Preferably, though, somewhat lower levels of UV initiators may be used, e.g., from 0.1-2.5 weight percent, preferably 0.5-1.0 weight percent, UV initiator, based on total weight of the phase in which it is present.

Initiators are available commercially, such as Vazo™ initiators, which typically indicate a decomposition temperature for the initiator, or the 10 hour half-life temperature of the respective initiator. Preferably the initiator is selected to have a decomposition point of 50° C. or higher. Blends of initiators can also be employed. Usefully multiple initiators are employed, either as a blend in the oil phase, or in either of the oil or water phases or both. When a blend or combination of initiators is employed they are selected so as to stagger the decomposition temperatures to coincide with the various steps of the capsule wall formation: e.g., prepolymerization, wall formation and hardening or polymerizing of the capsule wall material. For example, the oil phase can contain a first initiator that decomposes at 55° C. and is selected to promote the oil phase (meth)acrylate oligomer/ prepolymer formation, the oil phase may also contain a second initiator, one that decomposes at 65° C. which aids in polymerization of the aforementioned oil phase (meth) acrylate oligomer/prepolymer to initiate forming the capsule wall material. Optionally, a third initiator may be contained in the oil phase or present in the water phase that decomposes at 85° C. and which facilitates polymerization or full cure of the capsule wall material. The amount of each initiator can be typically as low as 0.1 weight percent or as high as 10 weight percent.

By selection of initiators and the amounts used and/or the time for which they are exposed to the conditions which generate the free radicals, it is possible to effect control or more control over the wall formation process and, in turn, the thickness and properties of the capsule wall. For example, one may use little or less initiator in a phase so as to avoid excess oligomerization or prepolymerization of the (meth)acrylate monomers and oligomers. Alternatively, and/ or in addition thereto, one may terminate the conditions that decompose the initiator so as to stop the generation of free radicals to likewise stop the polymerization process.

Encapsulated benefit agents may be manufactured and are subsequently coated with a material to reduce the rate of leakage of the benefit agent from the microcapsules when the microcapsules are subjected to a bulk environment containing, for example, surfactants, polymers, and solvents. Non-limiting examples of coating materials that can serve as bather materials include materials selected from the group consisting of polyvinyl pyrrolidone homopolymer, and its various copolymers with styrene, vinyl acetate, imidazole, primary and secondary amine containing monomers, methyl acrylate, polyvinyl acetal, maleic anhydride; polyvinyl alcohol homopolymer, and its various copolymers with vinyl acetate, 2-acrylamide-2-methylpropane sulfonate, primary and secondary amine containing monomers, imidazoles, methyl acrylate; polyacrylamides; polyacrylic acids; microcrystalline waxes; styrene-butadiene latex; paraffin waxes; modified polysaccharides such as waxy maize or dent corn starch, octenyl succinated starches, derivatized starches such as hydroxy ethylated or hydroxy propylated starches, high amylose starches, gel forming retrogradable starches, pregelatinized starches, carrageenan, guar gum, sodium alginate, pectin, xanthan gum; modified celluloses such as hydrolyzed cellulose acetate, hydroxy propyl cellulose, carboxymethyl hydroxyethyl cellulose, hydroxyethyl cellulose, methyl cellulose, microcrystalline cellulose, acid-hydrolyzed microcrystalline cellulose to yield cellulose nanocrystals, and the like; modified proteins such as gelatin, casein; hydrogenated and non-hydrogenated polyalkenes; fatty acids; polyacrylic acid; hardened shells such as, gelatinpolyphosphate, polyvinyl alcohol crosslinked with sodium tetraborate or gluteraldehyde; latexes of styrene-butadiene, ethyl cellulose, silica and modified silica; inorganic materials such as clays including magnesium silicates, aluminosilicates; sodium silicates, and the like; and mixtures thereof. Such materials can be obtained from CP Kelco Corp. of San Diego, Calif., USA; Degussa AG or Dusseldorf, Germany; BASF AG of Ludwigshafen, Germany; Rhodia Corp. of Cranbury, N.J., USA; Baker Hughes Corp. of Houston, Tex., USA; Hercules Corp. of Wilmington, Del., USA; Agrium Inc. of Calgary, Alberta, Canada, ISP of New Jersey U.S.A, Purdue University, Indiana, USA.

Suitable equipment for use in the processes disclosed herein may include continuous stirred tank reactors, homogenizers, turbine agitators, recirculating pumps, paddle mixers, ploughshear mixers, ribbon blenders, vertical axis granulators and drum mixers, both in batch and, where available, in continuous process configurations, spray dryers, and extruders. Such equipment can be obtained from Lodige GmbH (Paderborn, Germany), Littleford Day, Inc. (Florence, Ky., U.S.A.), Forberg AS (Larvik, Norway), Glatt Ingenieurtechnik GmbH (Weimar, Germany), Niro (Soeborg, Denmark), Hosokawa Bepex Corp. (Minneapolis, Minn., USA), Arde Barinco (New Jersey, USA).

In one aspect, a slurry that may comprise any of the microcapsules disclosed in the present specification is disclosed. Said slurry may be combined with an adjunct ingredient to form a composition for various end use applications.

In one aspect of said slurry, one or more processing aids are selected from the group consisting of water, aggregate inhibiting materials such as divalent salts, microcapsule suspending polymers, and mixtures thereof. Examples of aggregate inhibiting materials include salts that can have a charge-shielding effect around the microcapsule, such as magnesium chloride, calcium chloride, magnesium bromide, magnesium sulfate, and mixtures thereof. Examples of microcapsule suspending polymers include polymers such as xanthan gum, carrageenan gum, guar gum, shellac, alginates, chitosan; cellulosic materials such as carboxymethyl cellulose, hydroxypropyl methyl cellulose, cationically charged cellulosic materials; polyacrylic acid; polyvinyl alcohol; hydrogenated castor oil; ethylene glycol distearate; and mixtures thereof.

In one aspect, said slurry may comprise one or more processing aids, selected from the group consisting of water, aggregate inhibiting materials such as divalent salts; microcapsule suspending polymers such as xanthan gum, guar gum, carboxy methyl cellulose.

In one aspect of the aforementioned slurry said one or more carriers may be selected from the group consisting of polar solvents, including but not limited to, water, ethylene glycol, propylene glycol, polyethylene glycol, glycerol; non-polar solvents, including but not limited to, mineral oil, perfume raw materials, silicone oils, hydrocarbon paraffin oils, and mixtures thereof.

In one aspect of said slurry, said slurry may comprise a deposition aid that may comprise a polymer selected from the group comprising: polysaccharides, in one aspect, cationically modified starch and/or cationically modified guar; polysiloxanes; poly diallyl dimethyl ammonium halides; copolymers of poly diallyl dimethyl ammonium chloride and polyvinyl pyrrolidone; a composition comprising polyethylene glycol and polyvinyl pyrrolidone; acrylamides; imidazoles; imidazolinium halides; polyvinyl amine; copolymers of poly vinyl amine and N-vinyl formamide; polyvinylformamide, polyvinyl alcohol; polyvinyl alcohol crosslinked with boric acid; polyacrylic acid; polyglycerol ether silicone crosspolymers; polyacrylic acids, polyacrylates, copolymers of polyvinyl amine and polyvinyl alcohol oligomers of amines, in one aspect a diethylenetriamine, ethylene diamine, bis(3-aminopropyl)piperazine, N, N-bis-(3-aminopropyl)methylamine, tris(2-aminoethyl)amine and mixtures thereof; polyethyleneimine, a derivatized polyethyleneimine, in one aspect an ethoxylated polyethyleneimine; a polymeric compound comprising, at least two moieties selected from the moieties consisting of a carboxylic acid moiety, an amine moiety, a hydroxyl moiety, and a nitrile moiety on a backbone of polybutadiene, polyisoprene, polybutadiene/styrene, polybutadiene/acrylonitrile, carboxyl-terminated polybutadiene/acrylonitrile or combinations thereof; pre-formed coacervates of anionic surfactants combined with cationic polymers; polyamines and mixtures thereof. Said slurry may also comprise optionally an anionic, cationic or neutral surfactant.

In one aspect, an agglomerate that comprises said microcapsules and a second material is disclosed.

In one aspect of said agglomerate, said second material may comprise a material selected from the group consisting of silicas, citric acid, sodium carbonate, sodium sulfate, sodium chloride, and binders such as sodium silicates, modified celluloses, polyethylene glycols, polyacrylates, polyacrylic acids, zeolites and mixtures thereof.

Number weighted particle size is a measurement giving equal weighting to a particle irrespective of its size. Coulter techniques and light obscuration can be used to count particles one by one and to report the size present.

The median is the size at which half of the particles are below and half are above. On a cumulative distribution $d_{50}$ is the median.

EXAMPLES

In the following examples, the abbreviations correspond to the following materials:

TABLE 1

| | Company/City | |
|---|---|---|
| VA-501 | Wako Specialty Chemicals, Richmond, VA | 4,4'-azobis (4-cyanovaleric acid) |
| CD9055 | Sartomer Company, Exton, PA | Carboxylic acid monofunctional acrylate monomer |
| TBAEMA | Sigma Aldrich, St. Louis, MO | 2-(tert-butylamino) ethyl methacrylate |
| Vazo 67 | E.I. duPont, Wilmington, DE | 2,2'-azobis (2-methylbutane nitrile) |
| IPM | Millipore Sigma, St. Louis, MO | Isopropyl myristate |

Figure 2:
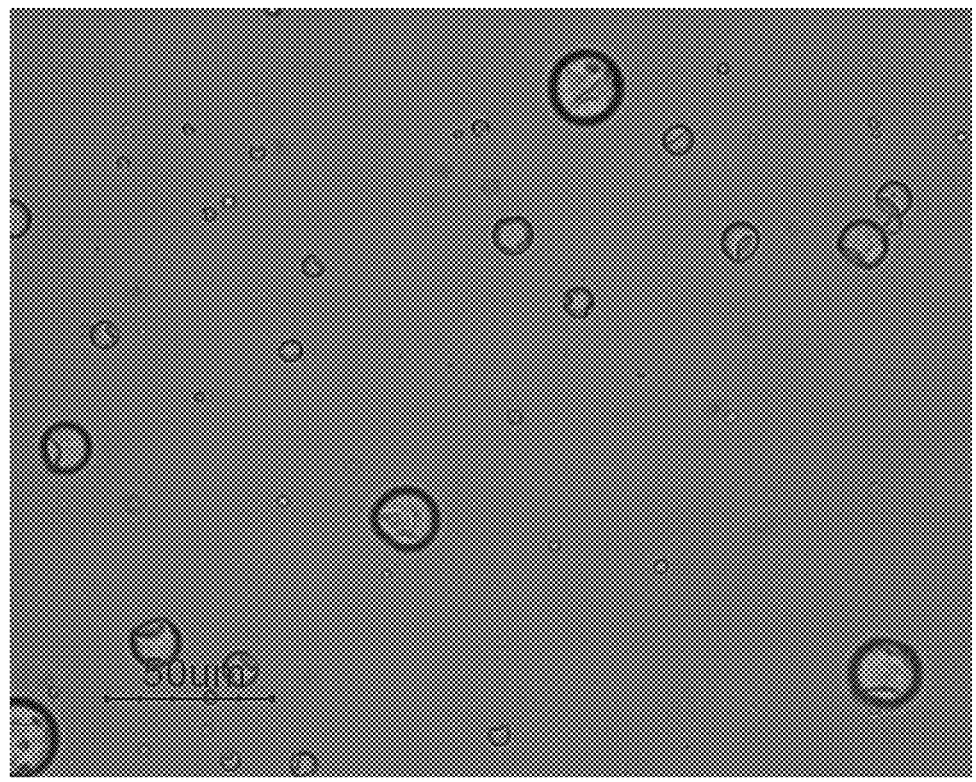
FIG. 2 is a photomicrograph of microcapsules with 0.0% aluminum sulfate of Example 1.
Figure 3:
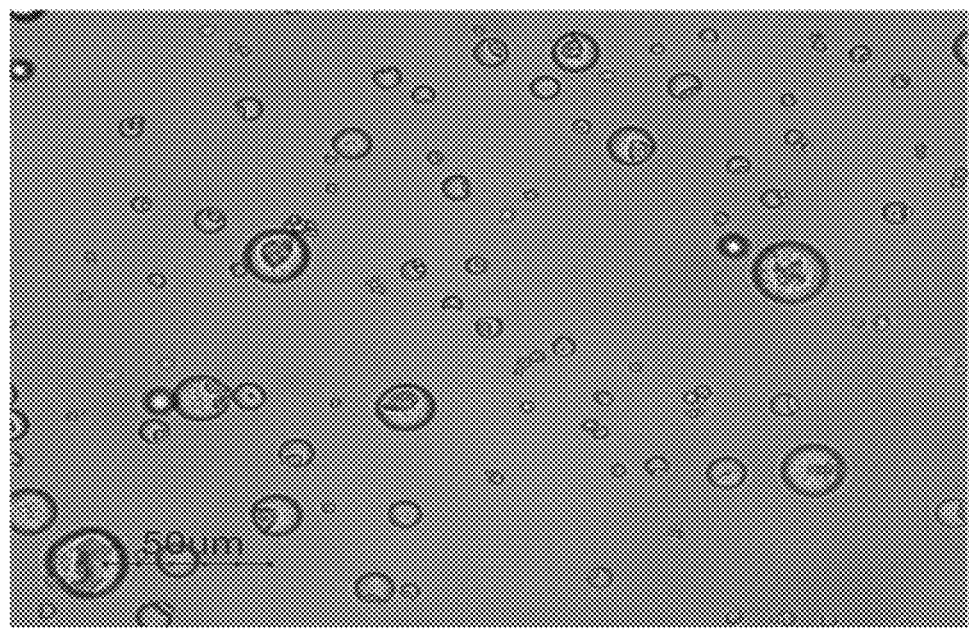
FIG. 3 is a photomicrograph of microcapsules with 1.4% aluminum sulfate of Example 2.
Figure 4:
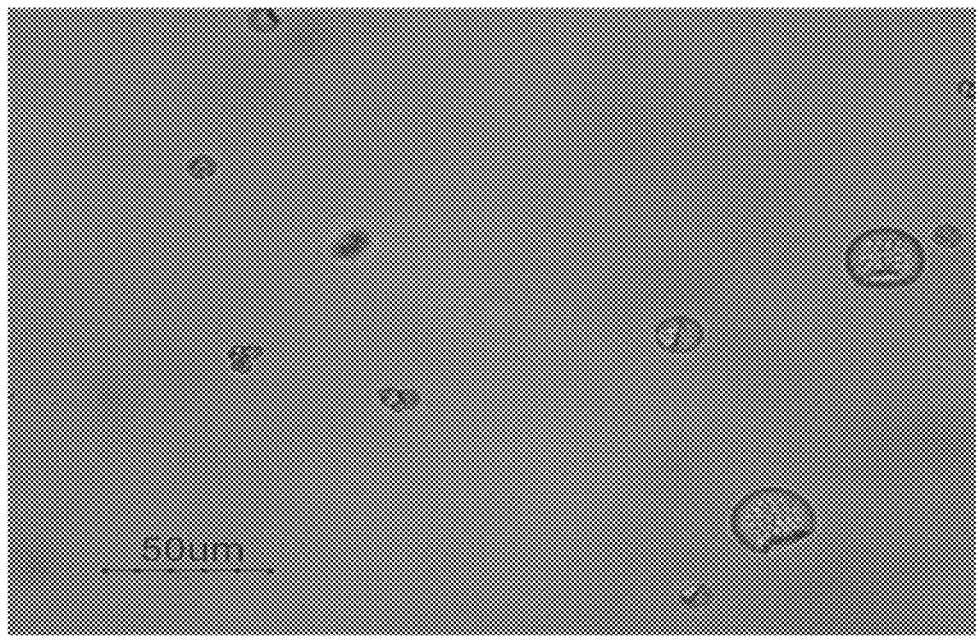
FIG. 4 is a photomicrograph of microcapsules with 2.7% aluminum sulfate of Example 3.
Figure 5:
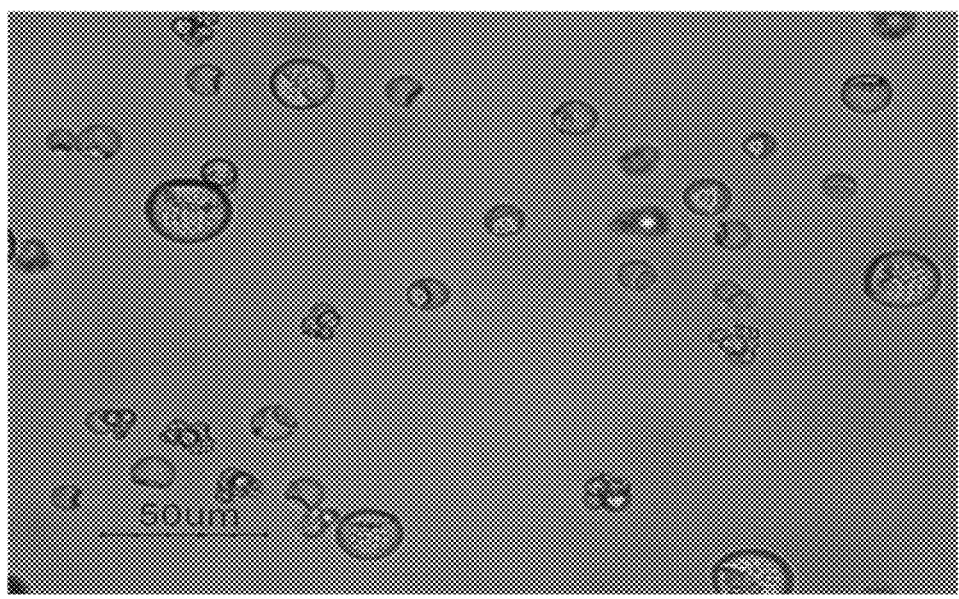
FIG. 5 is a photomicrograph of microcapsules with 4.1% aluminum sulfate of Example 4.
Figure 6:
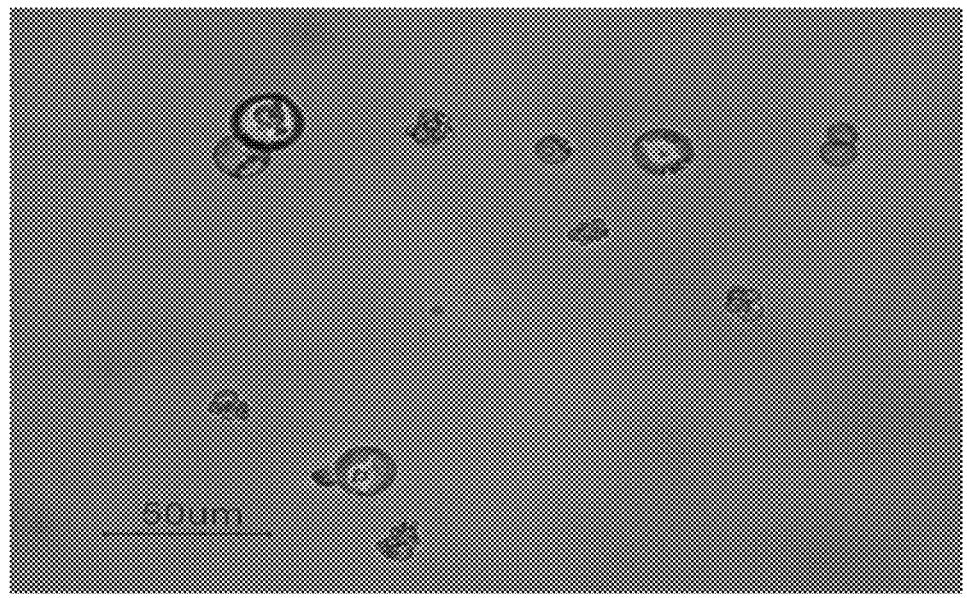
FIG. 6 is a photomicrograph of microcapsules with 5.4% aluminum sulfate of Example 5.
Figure 7:
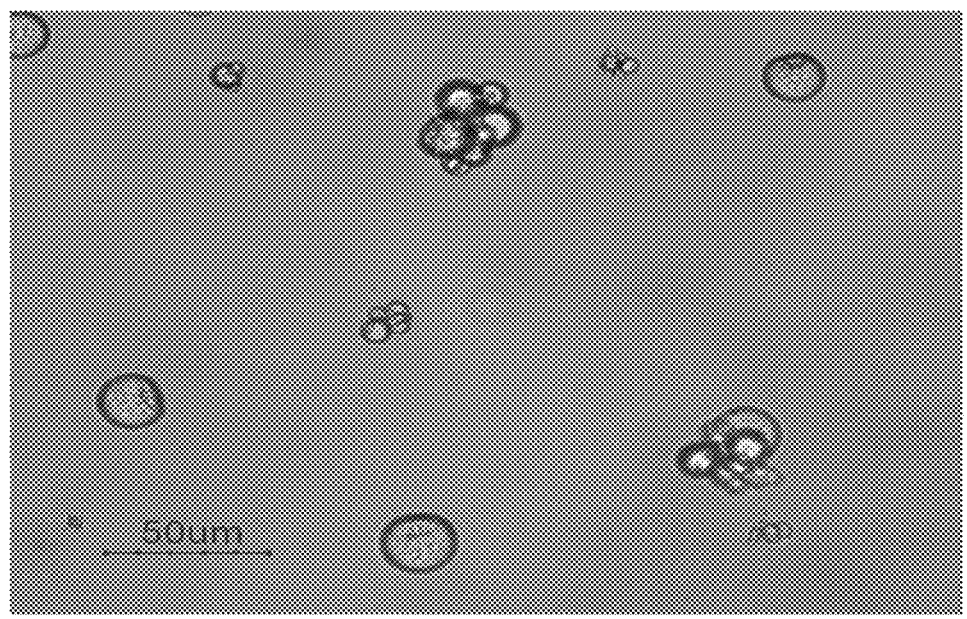
FIG. 7 is a photomicrograph of microcapsules with 6.7% aluminum sulfate of Example 6.
Figure 8:
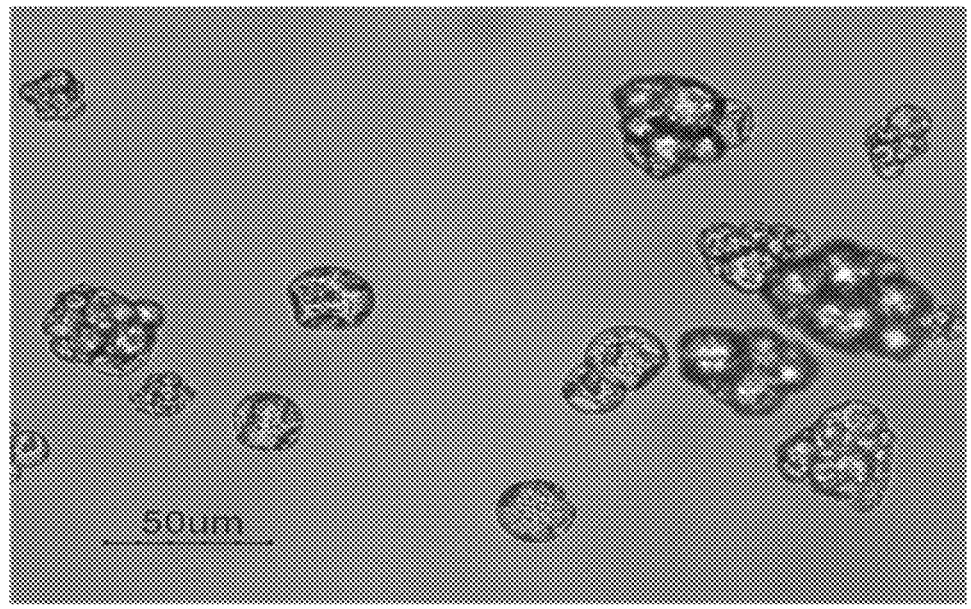
FIG. 8 is a photomicrograph of microcapsules with 12.1% aluminum sulfate of Example 7.

Aluminum sulfate was added and after milling of the emulsion. A succession of heating steps was used: heated to 75° C., held at 75° C. for 5 hours, heated to 95° C., held at 95° C. for 7 hours, and cooled to room temperature. The detailed experiment procedure is listed in Table 2. The number weighted median particle size distribution (PSD) shifted from 0.84 microns for the control to 20.78 microns for 12.1% aluminum sulfate as seen in FIG. 1 and Table 3. The size of the aggregated clusters can be selectively controlled by using different levels of aluminum sulfate, as shown in Table 3. When 1.4% aluminum sulfate was used in the system, the capsule clusters were formed by selectively aggregating capsules less than 2 microns. The aluminum cations were able to aggregate capsules less than 5 microns when its loading increased to 2.7%. Higher levels of aluminum cations in the system result in larger clusters, as illustrated in FIG. 2.

TABLE 2

Example composition and procedure

| Component | Solids % | Dry % | Wet % | Lab wet (g) | Dry wgt (g) |
|---|---|---|---|---|---|
| Water Phase | | | | | |
| Water | 0 | | 40.41 | 221.76 | 0.64 |
| 5% polyvinyl alcohol | 5 | 1.58 | 12.76 | 70.03 | 0.05 |
| 21% NaOH | 21.5 | 0.12 | 0.22 | 1.20 | 0.20 |
| VA-501 | 100 | | 0.20 | 1.10 | |
| Oil Phase II | | | | | |
| Perfume | 100 | 50.73 | 20.50 | 112.50 | 20.50 |
| IPM | 100 | 16.91 | 6.83 | 37.50 | 6.83 |
| Vazo 67 | 100 | 0.45 | 0.18 | 1.00 | 0.18 |
| VA-501 | 100 | 0.36 | 0.15 | 0.80 | 0.15 |
| Oil Phase I | | | | | |
| Perfume | 100 | 16.91 | 6.83 | 37.50 | 6.83 |
| TBAEMA | 100 | 0.10 | 0.04 | 0.22 | 0.04 |
| CD9055 | 100 | 0.10 | 0.04 | 0.22 | 0.04 |
| Tris (2-hydroxy ethyl) isocyanurate triacrylate | 100 | 8.12 | 3.28 | 18.00 | 3.28 |
| Aluminum Sulfate | 20 | 4.10 | 8.29 | 15.50 | 1.66 |
| Adjust to 500 g | | | | | |
| Acticide | 5 | 0.03 | 0.27 | 1.50 | 0.01 |
| Total | | 100.00 | 100.00 | 548.83 | 40.41 |

| Duration (min) | Procedure |
|---|---|
| 30 | Mix Oil Phase II in reactor |
| | Heat Oil Phase II to 35° C. with N₂ blanket on |
| | Mix a low speed (120 rpm) |
| 45 | Oil Phase II heated to 70° C. |
| 45 | Mix Water Phase in separate container |
| 45 | Oil Phase II held at 70° C. |
| 75 | Oil Phase II cooled to 50° C. |
| 30 | Begin Oil Phase I at room temperature (first 3 components) |
| 15 | Add SR368 into Oil Phase I; after it dissolves, cool to room temperature |
| 2 | Add Oil Phase I into Oil Phase II |
| 10 | Mix Oil Phases |
| 3 | Add Water Phase into Oil |
| 60 | Begin milling at 50° C.; mill to 18 microns |
| 2 | Reduce mill speed |
| 2 | Add Aluminum sulfate |
| 300 | Heat to 75° C. and maintain temperature |
| 420 | Heat to 95° C. and maintain temperature |

The microcapsules at various loading levels of aluminum sulfate clustered and performed better in olfactive properties. The aggregates or clusters enable a fragrance to be perceived over longer time periods. The clusters are believed to retain more scent, making available longer.

Clusters were not seen to form with cation addition subsequent to microcapsule formation and particle size distribution did not change. Polyvalent cation added before microcapsule wall polymerization is believed to enable polyvalent cation incorporation into the capsule wall and promote formation of capsule clusters, and not attributed to electrostatic or charge interactions. The clustering is not prone to disaggregation and exhibits a degree of permanency. Clustering is desirable for better deposition or positioning microcapsules spatially elevated when deposited on some surfaces.

Clustering was not seen in the examples when polyvalent cation addition was delayed to subsequent microcapsule wall polymerization.

The microcapsules at 4.1% aluminum sulfate loading were found to have a more pronounces positive zeta potential as compared to the control and as compared to addition subsequent to microcapsule wall polymerization.

Figure 9:
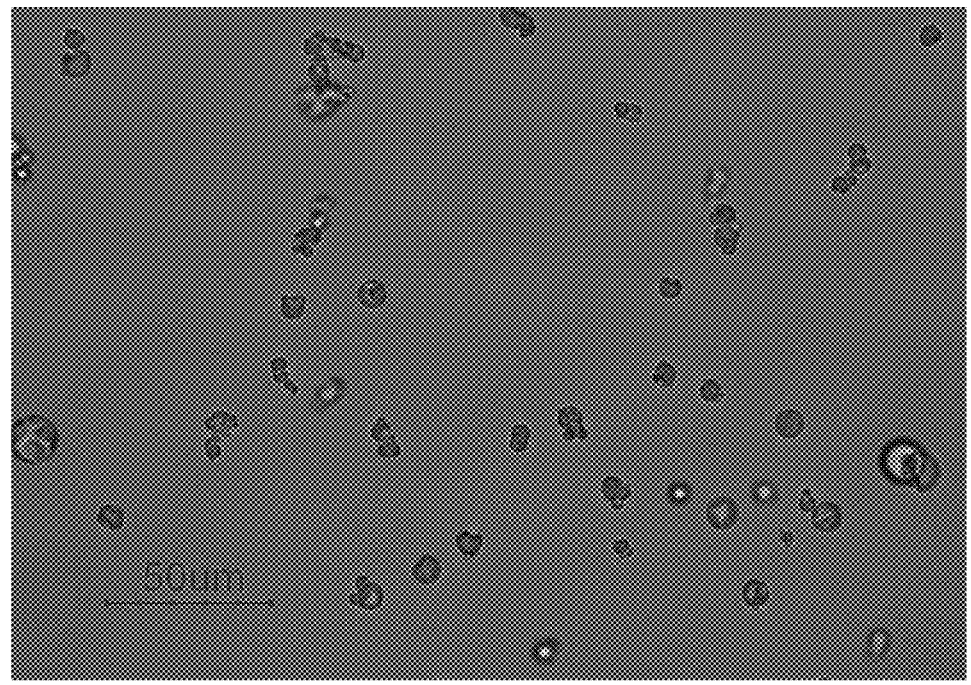
FIG. 9 is a photomicrograph of microcapsules with 1.4% zirconium sulfate of Example 12.
Figure 10:
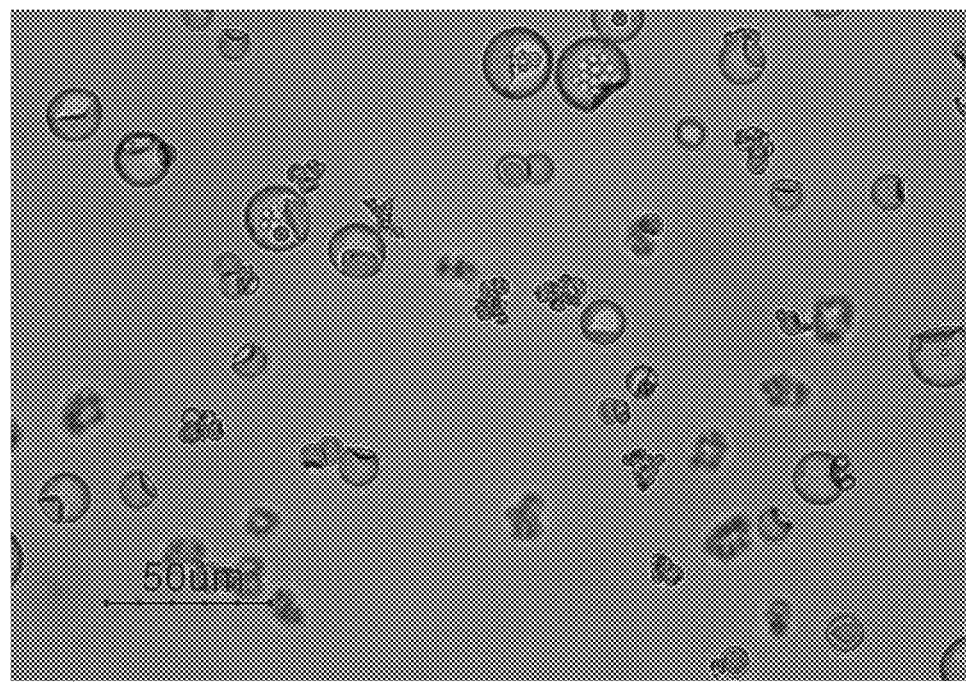
FIG. 10 is a photomicrograph of microcapsules with 1.4% ferric sulfate of Example 13.

Iron (III) and Zirconium (IV) aggregated microcapsules to form clusters, as shown in FIGS. 9 and 10. With 1.4% Fe (III) or 1.4% Zr(IV), the number of microcapsules less than 4 microns was reduced due to cluster formation.

Other salts, such as zirconium(IV) sulfate, iron(III) sulfate, manganese(II) sulfate, zinc(II) sulfate and magnesium (II) chloride were evaluated by adding the polyvalent salt before wall polymerization of the microcapsules. The number weighted particle size distribution information is listed in Table 3. Iron(III) and zirconium(IV) cations were able to aggregate microcapsules to form microcapsule clusters. With 1.4% Zr(IV) or 1.4% Fe(II) cations, the number of microcapsules less than 4 microns was substantially reduced by cluster formation. Sodium, manganese, magnesium, and zinc cations did not make significant impact on particle size and did not result in observable clusters.

TABLE 3

Particle Size and zeta potential of PAC Capsules with Varying Levels of Aluminum Sulfate

| | $Al_2(SO_4)_3$ level | Number Weighted Median Size (micron) | Volume Weighted Median Size (micron) | Zeta Potential at pH 3 (mV) | Zeta Potential at pH 5 (mV) |
|---|---|---|---|---|---|
| Example 1 | 0.0% | 0.84 | 18.06 | −0.4 | −0.8 |
| Example 2 | 1.4% | 4.81 | 16.25 | 2.2 | 0.1 |
| Example 3 | 2.7% | 8.34 | 17.23 | 1.0 | 0.6 |
| Example 4 | 4.1% | 11.31 | 17.03 | 0.5 | 2.2 |
| Example 5 | 5.4% | 11.71 | 18.27 | 0.2 | 1.3 |
| Example 6 | 6.7% | 14.80 | 22.29 | 0.5 | 1.5 |
| Example 7 | 12.1% | 20.78 | 40.96 | 0.8 | 0.5 |

TABLE 4

Particle Size of microcapsules with salts added before polymerization.

| Example Description | Number Weighted Median Size | Volume Weighted Median Size | Zeta Potential at pH 3 (mV) | Zeta Potential at pH 5 (mV) |
|---|---|---|---|---|
| Example 4.1% $Na_2SO_4$ 8 | 1.66 | 14.97 | −0.18 | −0.45 |
| Example 4.1% $AlCl_3$ 9 | 12.27 | 18.92 | 0.51 | 12.15 |
| Example 4.1% Polyaluminum Chloride 10 | 8.91 | 20.06 | 1.23 | 12.22 |
| Example 4.1% $MgCl_2$ 11 | 0.90 | 15.69 | −0.43 | −0.44 |
| Example 1.4% $Zr(SO_4)_2$ 12 | 8.34 | 17.03 | 0.21 | −1.16 |
| Example 1.4% $Fe_2(SO_4)_3$ 13 | 7.42 | 16.83 | 1.99 | 0.80 |
| Example 1.4% $Mn\ SO_4$ 14 | 0.85 | 17.23 | −1.44 | −0.26 |
| Example 1.4% $Zn\ SO_4$ 15 | 0.85 | 17.03 | −0.35 | −0.53 |

Unless otherwise indicated, all measurements herein are on the basis of weight and are metric units. All documents cited in the specification herein are, in relevant part, incorporated herein by reference for all jurisdictions in which such incorporation is permitted. The citation of any publication is for its disclosure prior to the filing date and should not be construed as an admission that such publication is prior art or that the present invention is not entitled to antedate such publication by virtue of prior invention. To the extent that any meaning or definition of a term in this document conflicts with any meaning or definition of the same term in a document incorporated by reference, the meaning or definition assigned to that term in this document shall govern.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Uses of singular terms such as "a," "an," are intended to cover both the singular and the plural, unless otherwise indicated herein or clearly contradicted by context. The terms "comprising," "having," "including," and "containing" are to be construed as open-ended terms. Any description of certain embodiments as "preferred" embodiments, and other recitation of embodiments, features, or ranges as being preferred, or suggestion that such are preferred, is not deemed to be limiting. All methods described herein can be performed in any suitable order unless otherwise indicated herein or otherwise clearly contradicted by context. The use of any and all examples, or exemplary language (e.g., "such as") provided herein, is intended to illuminate the invention and does not pose a limitation on the scope of the invention. No unclaimed language should be deemed to limit the invention in scope. Any statements or suggestions herein that certain features constitute a component of the claimed invention are not intended to be limiting unless reflected in the appended claims.

The principles, preferred embodiments, and modes of operation of the present invention have been described in the foregoing specification. The invention which is intended to be protected herein, however, is not to be construed as limited to the particular forms disclosed, since these are to be regarded as illustrative rather than restrictive variations and charges can be made by those skilled in the art without departing from the spirit and scope of the invention.

What is claimed is:

1. A cluster of microcapsules comprising:
   two or more microcapsules comprising a core and shell, each microcapsule containing a beneficial core material, which is the same or different; and the shell comprising a free radical initiated polymeric wall material surrounding the core and a polyvalent cation binding the two or more microcapsules forming the cluster; the polymeric wall material comprising the reaction product of:
   a) from 0.1 to 15% by weight of an amine (meth)acrylate;
   b) from 0.1 to 15% by weight of an acid (meth)acrylate; and,
   c) from 99.8 to 60% of a multifunctional (meth)acrylate;
   wherein the microcapsules are substantially irreversibly agglomerated.

2. The cluster of microcapsules according to claim 1 wherein the cluster of microcapsules has a number weighted median particle size of the cluster of from 1.1 times to 75 times as compared to the number weighted median particle size of the constituent microcapsules.

3. The cluster of microcapsules according to claim 1 wherein the polyvalent cation is selected from the group consisting of Al(III), Zr(IV), Sn(IV) and Fe(III).

4. The cluster of microcapsules according to claim 1 wherein the polyvalent cation is at least 0.01% of the microcapsule by weight.

5. The cluster of microcapsules according to claim 1 wherein the cluster has a zeta potential of from −60 millivolts to +60 millivolts.

6. A cluster of microcapsules comprising: two or more microcapsules comprising a core and shell, each microcapsule containing a beneficial core material, which is the same or different; and the shell comprising a free radical initiated polymeric wall material surrounding the core and a polyvalent cation binding the two or more microcapsules forming the cluster; wherein the polymeric wall material of the microcapsule shell comprises (meth)acrylate polymer comprising a reaction product of either (A) (a) at least one oil soluble or dispersible amine (meth)acrylate, (b) at least one oil soluble or dispersible acidic (meth)acrylate or at least one oil soluble or dispersible simple acid or both, and (c) at least one oil soluble or dispersible multifunctional (meth)acrylate monomer or oligomer or (B) (a) at least one oil soluble or dispersible acidic (meth)acrylate, (b) at least one oil soluble or dispersible simple base, and (c) at least one oil soluble or dispersible multifunctional (meth)acrylate monomer or oligomer.

7. The cluster of microcapsules according to claim 6 wherein the (meth)acrylate polymer is a reaction product of (a) at least one oil soluble or dispersible amine (meth)acrylate, (b) at least one oil soluble or dispersible acidic (meth)acrylate or at least one oil soluble or dispersible simple acid or both, and (c) at least one oil soluble or dispersible multifunctional (meth)acrylate monomer or oligomer.

8. The cluster of microcapsules according to claim 1 wherein the microcapsule shell comprises in addition melamine resin with the (meth)acrylate polymer and wherein the melamine resin is derived from an aqueous phase and the (meth)acrylate polymer is derived from an oil phase, said (meth)acrylate polymer comprising the reaction product of either (A) (a) at least one oil soluble or dispersible amine (meth)acrylate, (b) at least one oil soluble or dispersible acidic (meth)acrylate or at least one oil soluble or dispersible simple acid or both, and (c) at least one oil soluble or dispersible multifunctional (meth)acrylate monomer or oligomer or (B) (a) at least one oil soluble or dispersible acidic (meth)acrylate, (b) at least one oil soluble or dispersible simple base, and (c) at least one oil soluble or dispersible multifunctional (meth)acrylate monomer or oligomer.

9. The cluster of microcapsules according to claim 1 wherein the (meth)acrylate polymer is a reaction product of (a) at least one oil soluble or dispersible amine (meth) acrylate, (b) at least one oil soluble or dispersible acidic (meth)acrylate or at least one oil soluble or dispersible simple acid or both, and (c) at least one oil soluble or dispersible multifunctional (meth)acrylate monomer or oligomer.

10. The cluster of microcapsules according to claim 1 wherein the cluster has a number weighted median size that is at least 1.1 times to 75 times greater than the number weighted median size of the microcapsules forming the cluster.

11. The cluster of microcapsules according to claim 1 wherein the cluster is cationic.

12. A process for preparing a cluster of microcapsules according to claim 1 encapsulating an oil phase, the cluster being substantially irreversibly agglomerated, the process comprising:
    dispersing an oil soluble amine modified polyfunctional polyvinyl monomer or oligomer and an oil soluble bi- or polyfunctional vinyl monomer or oligomer along with a free radical initiator and an organic acid and a core material into an internal phase oil;
    a first heating step comprising, heating for a time and temperature sufficient to pre-polymerize the amine modified polyfunctional polyvinyl monomer or oligomer and oil soluble bi- or polyfunctional vinyl monomer or oligomer;
    adding to the internal phase oil a water phase in excess comprising a dispersion in water of a polyacrylic or poly(meth)acrylic acid, a free radical initiator, and an emulsifying agent;
    emulsifying the oil phase into the water phase forming an emulsion of droplets of the oil phase dispersed in the water phase;
    heating the emulsion for a time and temperature sufficient to decompose the free radical initiator in the oil and water phases thereby forming microcapsule wall material at the interface of the water and oil phases, the microcapsules encapsulating the oil phase droplets;
    adding a polyvalent cation to the emulsion; and,
    further heating for a time sufficient to polymerize the wall material and agglomerate the wall material, the polyvalent cation being incorporated into the microcapsule wall, thereby forming the cluster of microcapsules.

13. The process according to claim 12 comprising adding the polyvalent cation after the emulsifying step.

14. The process according to claim 12 comprising adding a polyvalent cation selected from the group consisting of Al(III), Zr(IV) and Fe(III).

15. The process according to claim 12 wherein in the emulsifying step the droplets of the oil phase are comminuted to a particle size of from 0.1 to 150 microns.

16. The process according to claim 12 wherein the cluster of microcapsules formed has a zeta potential form −60 millivolts to +60 millivolts.

17. The process according to claim 12 wherein the cluster of microcapsules formed is cationic.

* * * * *